United States Patent [19]
Fischell

[11] Patent Number: 4,731,051
[45] Date of Patent: Mar. 15, 1988

[54] PROGRAMMABLE CONTROL MEANS FOR PROVIDING SAFE AND CONTROLLED MEDICATION INFUSION

[75] Inventor: Robert E. Fischell, Silver Spring, Md.

[73] Assignee: The Johns Hopkins University, Baltimore, Md.

[21] Appl. No.: 466,494

[22] Filed: Feb. 15, 1983

Related U.S. Application Data

[63] Continuation-in-part of Ser. No. 34,155, Apr. 27, 1979; Pat. No. 4,373,527.

[51] Int. Cl.⁴ ............................................. A61M 5/00
[52] U.S. Cl. ...................................... 604/67; 604/50; 604/891.1
[58] Field of Search ............... 128/DIG. 12, DIG. 13; 604/891, 131, 65–66, 31, 50, 67, 245

[56] References Cited

U.S. PATENT DOCUMENTS

| | | | |
|---|---|---|---|
| 3,923,060 | 12/1975 | Ellinwood, Jr. | 128/DIG. 13 |
| 4,037,598 | 7/1977 | Georgi | 128/DIG. 13 |
| 4,077,405 | 3/1978 | Haerten et al. | 128/DIG. 13 |
| 4,270,532 | 6/1981 | Franetzki et al. | 604/151 |
| 4,282,872 | 8/1981 | Franetzki et al. | 128/213 R |
| 4,308,866 | 1/1982 | Jelliffee et al. | 128/214 E |
| 4,373,527 | 2/1983 | Fischell | 128/260 |

FOREIGN PATENT DOCUMENTS 2127179  4/1984  United Kingdom .

OTHER PUBLICATIONS

"Microcomputer—Controlled Devices for Human Implantation", R. E. Fischell, APL Technical Digest.
"The SAS-A Telenetry System", M. R. Peterson, D. C. Zitterkopf, APL Technical Digest.

Primary Examiner—William E. Kamm
Assistant Examiner—F. Jaworski
Attorney, Agent, or Firm—Robert E. Archibald; Howard W. Califano

[57] ABSTRACT

An implantable programmable infusion pump (IPIP) is disclosed and generally includes: a fluid reservoir filled with selected medication; a pump for causing a precise volumetric dosage of medication to be withdrawn from the reservoir and delivered to the appropriate site within the body; and, a control means for actuating the pump in a safe and programmable manner. The control means includes a microprocessor, a permanent memory containing a series of fixed software instructions, and a memory for storing prescription schedules, dosage limits and other data. The microprocessor actuates the pump in accordance with programmable prescription parameters and dosage limits stored in the memory. A communication link allows the control means to be remotely programmed. The control means incorporates a running integral dosage limit and other safety features which prevent an inadvertent or intentional medication overdose. The control means also monitors the pump and fluid handling system and provides an alert if any improper or potentially unsafe operation is detected.

112 Claims, 22 Drawing Figures

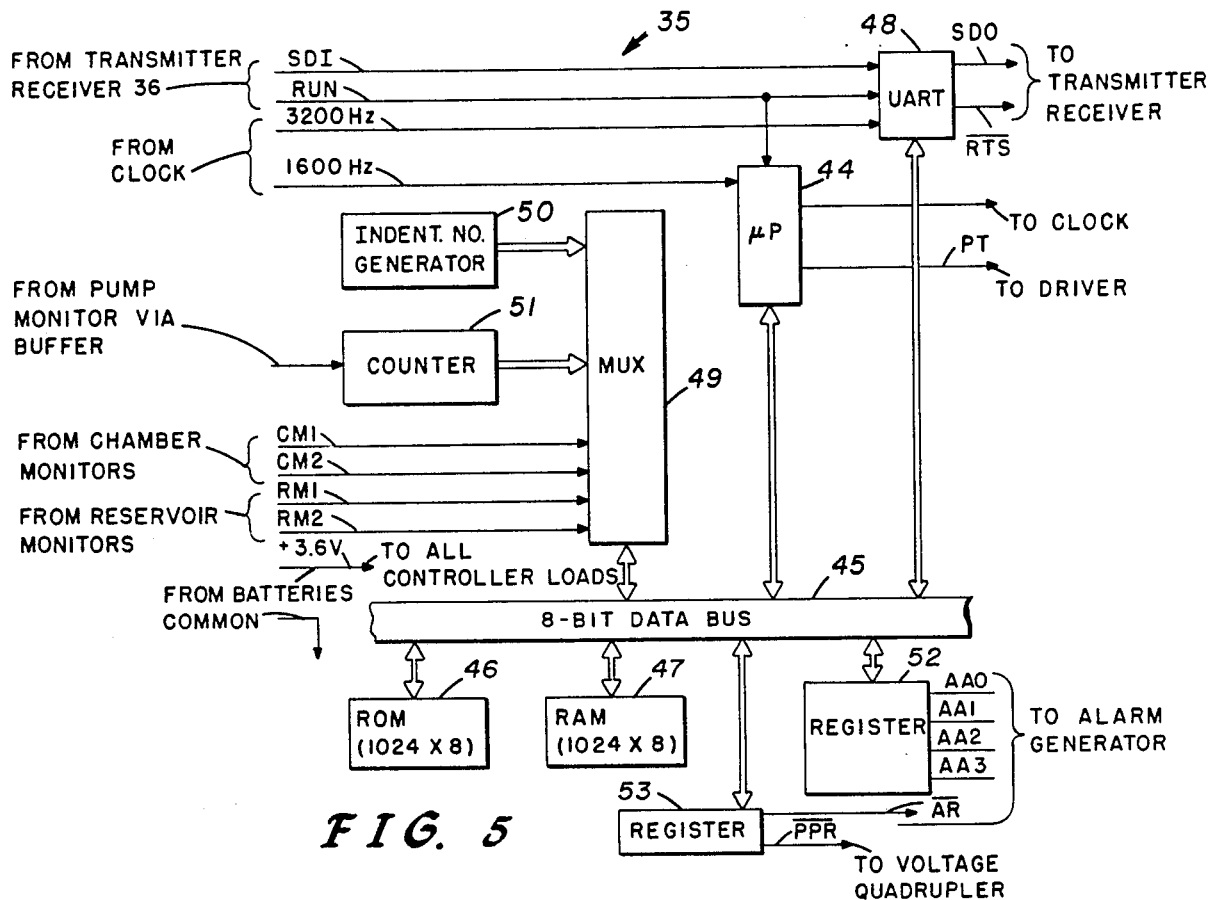

FIG. 5

| CATEGORY | ITEM DESCRIPTION | RAM ALLOCATION | |
|---|---|---|---|
| | | NUMBER OF BYTES | CATEGORY SUBTOTAL |
| PARAMETER DEFINITION | SUPPLEMENTAL MEDICATION DELIVERY SCHEDULES<br>BASAL MEDICATION DELIVERY SCHEDULE<br>3-HOUR DOSE LIMIT<br>24-HOUR DOSE LIMIT<br>ALARM AMPLITUDE<br>INITIALIZATION | 192<br>12<br>1<br>1<br>1<br>44 | 251 |
| UTILIZATION RECORD | HOUR PUMP RESPONSE COUNTS<br>CUMULATIVE PUMP RESPONSE COUNTS<br>DAILY PUMP STIMULUS COUNT<br>CUMULATIVE PUMP STIMULUS COUNT<br>CUMULATIVE DIRECTIVE ACCEPTANCE COUNTS<br>CUMULATIVE DIRECTIVE REJECTION COUNTS<br>CUMULATIVE LIMIT COUNT<br>CUMULATIVE INHIBIT COUNT | 480<br>2<br>20<br>2<br>16<br>10<br>2<br>2 | 534 |
| WORKSPACE | MISCELLANEOUS | 239 | 239 |
| TOTAL RAM CAPACITY | | 1024 | 1024 |

FIG. 6

PROGRAMMABLE CONTROL MEANS FOR PROVIDING SAFE AND CONTROLLED MEDICATION INFUSION

STATEMENT OF GOVERNMENTAL INTEREST

The invention described herein was made in the performance of work under NASA Contract No. NDPR S-63983B and is subject to the provisions of Section 305 of the National Aeronautics and Space Act of 1958 (72 Stat. 435; 42 U.S.C. 2457).

CROSS-REFERENCE TO RELATED APPLICATION

This is a continuation-in-part of patent application, Ser. No. 34,155, filed on Apr. 27, 1979, now U.S. Pat. No. 4,373,527.

BACKGROUND AND/OR ENVIRONMENT OF THE INVENTION

1. Field of the invention

The present invention pertains to a control means incorporating a microprocessor for actuating a pump in accordance with programmable prescription parameters and dosage limits. The disclosed control means incorporates running integral dosage limits and other safety features which prevent an inadvertent or intentional medication overdose.

2. Description of the Comtemporary and/or Prior Art

Various techniques and devices have been suggested and are currently under study which addresses the problem of dispensing a drug or other medicative liquid into the living body. In these techniques and devices, however, redundant safety features and flexibility achieved by programming dosage inputs are rarely contemplated.

One liquid infusion device discussed in U. S. Pat. No. 4,007,405 by Haerten et al comprises a controlable dosing arrangement which provides for human operator interaction. A syringe forces liquid through a pressure valve into a supply reservoir and a bellows pump forces the drug from the reservoir through a flow limiter into the body. This device fails to address various safety problems such as leakage, excessive pumping, and excessive requests for drugs. No provision exists for detecting leaks in the device, for signalling malfunctions, for restricting the number of or quantity of drug doses, or for monitoring proper operation of the device.

Like Haerten et al, U. S. Pat. No. 3,692,027 by Ellinwood teaches an implanted, self-powered drug dispenser having a bellows pump which is fed through and expels the drug through valves, in particular one-way valves. The Ellinwood device is not programmable; it varies dosage by opening and closing portals or selecting a dose or medication from one of a plurality of pumps having different dosage volumes and/or different medications stored therein. Safety redundancy such as pressure integrity checks during filling, leakage problems, patient and doctor interaction with the dispenser, and dosage input programming are not considered.

SUMMARY OF THE INVENTION

The present application describes a programmable control means for actuating a pump thereby causing medication to be infused in accordance with programmable prescription parameters and dosage limits. The implantable programmable infusion pump (IPIP) generally contains: (1) a fluid reservoir filled with a selected medication which is refillable using a hypodermic needle; (2) a catheter for channeling medication dosages to the proper site within the patient's body; (3) a pump for causing a precise volumetric dosage of medication to be withdrawn from the reservoir and to be delivered via the catheter to the appropriate site within the patient's body with each pump actuation; and (4) a control means for actuating the pump in a proper and programmable manner.

The control means contains a transmitter/receiver which enables it to be remotely programmed by a hand held patient programming unit (PPU) and a medication programming unit (MPU). The PPU is operated by the patient and allows the patient to self-medicate. The MPU is operated by the physician and enables him to program basal and supplemental prescription schedules and set dosage and control limits. The physician using the MPU programs a basal delivery schedule, several supplemental prescription schedules, and various dosage limits and control limits. The PPU is limited in its programming capability and a patient can merely choose to deliver a full or half basal rate, select on of the several pre-programmed supplemental prescription schedules, inhibit pump activity, or countermand previous directives.

This drug infusion system provides the patient with the flexibility of increasing or decreasing dosages in accordance with physiological or activity levels. For example, if the pump delivers insulin, a patient would wish to increase dosages immediately after consuming a meal, so that a high post-prandial insulin profile is obtained. However, this flexibility of dosage programming by the physician and self-medication by the patient creates certain safety considerations. Since the implantable programmable infusion pump (IPIP) is remotely programmable by both the patient and physician, and since it has a potential of delivering a lethal dosage of medication, the controller must be able to accurately control medication delivery and it must have safety features to prevent inadvertent or intentional misuse.

Therefore, a first object is to provide a basal delivery means for actuating the pump in accordance with a programmed basal prescription schedule. Only the physician using the MPU has the capability of programming the basal rate. The patient using the PPU can require a half or full basal delivery, or can inhibit pump actuation for a certain set period of time. The physician can program patient medication constraints which can further limit or remove entirely the patient's ability to modify the basal prescription schedule.

A second object is to provide a supplemental prescription schedule delivery means for actuating the pump in accordance with at least one supplemental prescription schedule. Again, only the physician can program the allowable supplemental prescription schedule. The patient using the PPU can merely choose one of the supplemental prescription schedules previously programmed by the physician. The supplemental prescription delivery means also double checks the supplemental prescription schedule programmed by the physician to assure that physician's programming errors do not inadvertently produce an inappropriate supplemental prescription schedule.

A third objective of the present invention is to provide a means for inhibiting pump actuations if a certain dosage rate limit is exceeded. A running integral dosage limit means sums the number of pump actuations which occur during the most recent shifting time window of a pre-selected length and inhibits pump actuation when such sum exceeds a programmable running integral dosage limit. The preferred embodiment utilizes both a 3-hour shifting window of time during which the pump count cannot exceed a 3-hour running integral dosage limit and a 24-hour shifting window of time during which the pump count cannot exceed a 24-hour running integral dosage limit. The 3-hour and 24-hour running integral dosage limits are programmable by the physician in accordance with a particular patient's physiology.

A fourth object is to provide a hardwired digital integrating rate limiter to back up the running integral dosage limiter means. The digital integrating rate limiter will inhibit pump actuation when a maximum dosage envelope is exceeded. The digital integrating rate limiter consists of an updown counter, a separate auxiliary clock, and a means to count actual pump actuations. The digital integrating rate limiter allows a maximum basal rate as well as a maximum delivery of medication at any particular time. Although the digital integrating rate limiter is utilized in the preferred embodiment as a backup system, in certain applications it could function independently.

A fifth object of the invention is to provide a "double handshake" means to assure that spurious or intefering signals are prevented from modifying prescription commands. After the transmitter/receiver detects a transmitted code, the controller checks for a valid 8-bit selection code. If a valid selection code is received, the controller uses the transmitter/receiver to retransmit the selection code back to the MPU or PPU. The MPU or PPU will verify that the selection code received is the one it had sent and transmits an execution code. Only if a valid and timely 8-bit execution code is received will the controller proceed to deliver medication in accordance with the selection code. This method of obtaining a secure communication is known to those versed in the art as a "double handshake" communication means.

A sixth object of the invention is to record system utilization and performance data which enables the physician to determine the effectiveness of the patient's self-medication and evaluate pump performance. The controller includes a random access memory (RAM) which is used to store utilization and performance data. The controller records the number of pump actuations, the number of times a particular selection code was used to assign a supplemental prescription schedule or request half or full basal delivery or inhibit pump actuation or countermand current directives, and the number of unverifiable or inappropriate selection codes received by the controller. The controller also has several ports which allows it to receive information relative to the performance of the pump and the fluid handling system. In the preferred embodiment, the controller connects to a moisture detector, a reservoir fill indicator, and a pump actuation or fluid flow monitor. The controller records readouts from these monitors on a periodic basis so the physician can determine possible system malfunctions.

A seventh object of the invention is to detect system malfunctions and to alert the patient when a system malfunction or anomaly occurs. As mentioned previously, the controller receives information from chamber, reservoir and pump monitors. A software anomaly alerting means provides a monitor report at periodic intervals. The monitor report indicates: (1) detection of moisture; (2) whether the reservoir is empty or too full; (3) whether pump actuation commands from the basal delivery means and supplemental prescription delivery means are greater than or less than the actual pump actuation count; or (4) whether prescription data stored in RAM has been altered—i.e., by a cosmic ray particle, any other corpuscular radiation or power transient. If two consecutive monitor reports show the same anomaly, the controller will actuate an alarm means and alert the patient. In the preferred embodiment, the alarm means provides the patient with a noticeable subcutaneous electrical stimulation (tickle) or audio alarm.

An eighth object is to provide a software means for deterring operator error. The controller checks supplemental prescription schedules for inadvertent programming errors made by the physician before each supplemental prescription schedule is delivered by the delivery means. The control alerts the patient if an unusual request is made. Unusual requests include: (1) a request to deliver half basal rate, (2) a request to return to a full basal rate delivery; (3) a request for a one-hour pump inhibition, or (4) a request to countermand current directives. If an unusual request is selected, the controller will actuate the alarm means and alert the patient. The physician using the MPU can inhibit (i.e., disable) this safety feature if it proves unnecessary for a particular patient. The controller can also be programmed by the MPU to ignore any one or several of the PPU commands. This feature enables the physician to restrict the patient's ability to self-medicate.

A ninth object is to provide a software controller which includes: a microprocessor a random access memory (RAM) or its equivalent for storing prescription parameters, prescription limits, and utilization and performance data, and a read-only memory (ROM) or equivalent for storing in fixed form a list of software instructions which enables the microprocessor to provide the above discussed medication delivery and safety features.

These objects, as well as further objects and advantages will become apparent after reading the ensuing description of a non-limiting illustrative embodiment and reviewing the accompanying drawings. These dosage delivery and limiting features may be incorporated in an implantable or external infusion pump system.

BRIEF DESCRIPTION OF THE DRAWINGS

In order that the present invention may be more fully understood, it will now be described, by way of example, with reference to the accompanying drawings in which:

FIG. 5 is a block diagrammatic view of the IPIP controller illustrating the connection between the microprocessor, the random access memory (RAM) and the read only memory (ROM);

FIG. 6 is a table showing a typical RAM allocation schedule as taught by the invention;

DESCRIPTION OF THE INVENTION

Figure 1:
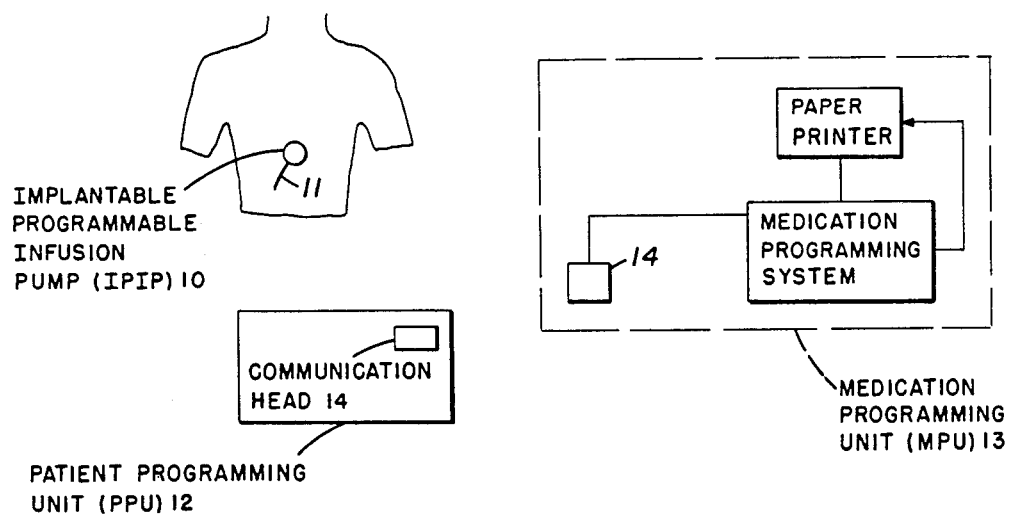
FIG. 1 is a block diagram of the invented medication infusion system.

FIG. 1 is a block diagrammatic view of the overall programmable implantable medication system (PIMS) which generally consists of: an implantable programmable infusion pump (IPIP) 10 which is implanted in a patient and provides a programmable and controlled release of medication (a catheter 11 allows the medication to be delivered to the appropriate site within the patient's body); a patient programming unit (PPU) 12 which is a hand held device used by the patient to communicate with the IPIP 10 for self medication; and, a medication programming unit (MPU) 13 which is used by the physician to program the IPIP with prescription parameters and dosage control limits. In this interactive medication infusion system, the physician can use the MPU to program a medication delivery schedule and the patient can use the PPU to fine tune the prescription to meet physiological needs. If the IPIP is delivering insulin, the PPU can be used to request supplemental medication delivery corresponding to food consumption or activity levels. A communication head 14 in both the PPU 12 and MPU 13 serves as transmitting and receiving antenna. The MPU is used by the physician to: (1) program the IPIP to deliver a basal prescription profile and record up to eight supplemental prescription profiles in the IPIP's memory; (2) set the 3-hour and 24-hour running integral dosage limits; (3) program the IPIP to ignore certain medication selections that the patient might send via the PPU; (4) set alarm criteria and timing constants; (5) check the chamber moisture and reservoir fill monitors; and (6) retrieve utilization and system performance records from the IPIP's memory.

Unlike the MPU 13, the PPU 12 is limited in its capacity to program the IPIP 10. The PPU 12 is used by the patient for self-medication, with the patient's ability to request medication dosages constrained to prevent inadvertent or intentional misuse. The PPU 12 can be used by the patient to: (1) request delivery of one of eight supplemental prescription schedules which were pre-programmed by the physician; (2) select half or full rate delivery of the pre-programmed basal prescription schedule; (3) inhibit pump operation for 1-hour periods; and, (4) countermand the current medication delivery directive.

Figure 2:
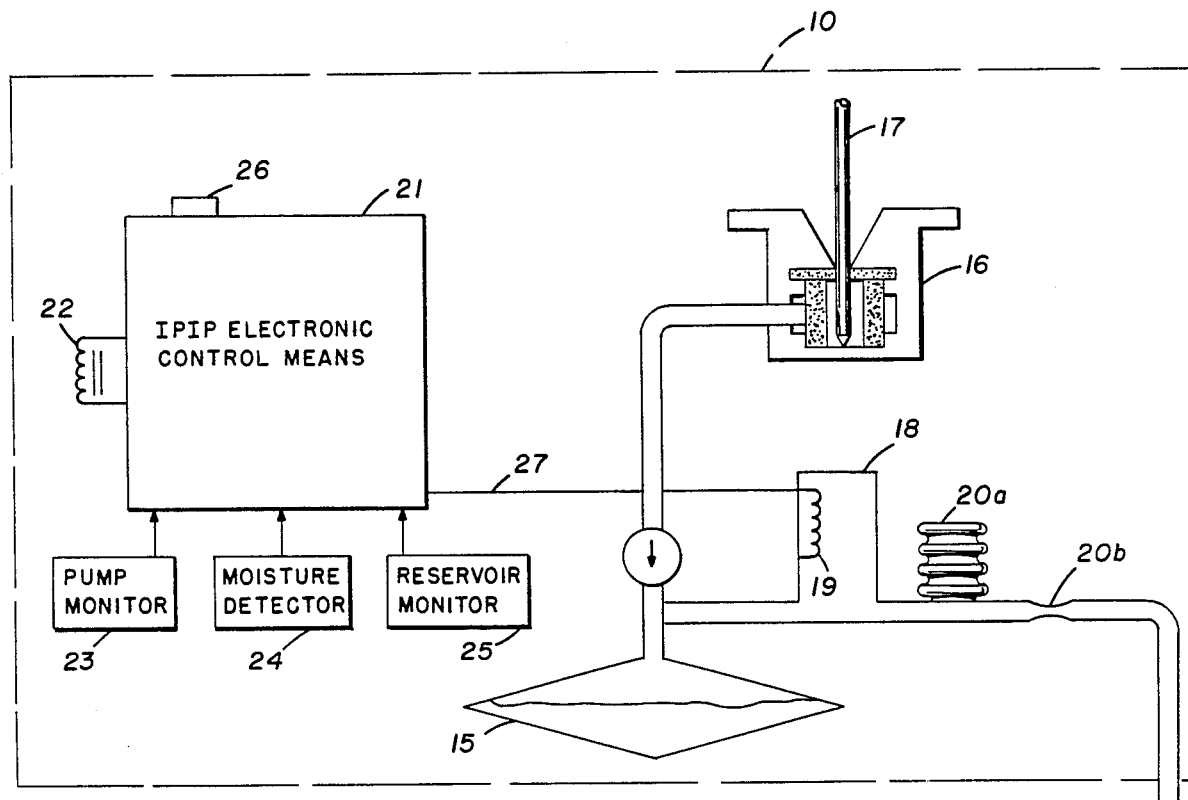
FIG. 2 is block diagram illustrating the electronic control means, pump, and fluid handling system.

FIG. 2 shows a block diagram of the overall implantable programmable infusion pump (IPIP) 10. The IPIP 10 generally comprises: (1) a medication reservoir 15 which stores selected medication to be delivered by the pump; (2) a refill entry port 16 which allows the physician to refill the implanted device using a hypodermic needle 17; (3) a pulsatile pump 18 which provides a single pulse of medication each time solenoid coil 19 is energized with an appropriate current pulse; (4) an accumulator 20a and a flow restrictor 20b which, working together, provide smoothing of the medication flow; (5) a catheter 11 for delivering medication to the appropriate site within the patient's body; and, (6) an electronic control means 21 which has the principle function of actuating the pulsatile pump 18 according to prescription schedules stored in the IPIP's memory.

The block representing the electronic control means 21 (FIG. 2) contains several ports which enables it to receive prescription parameters, monitor the fluid system, alert the patient to malfunctions, and actuate the pump. A pick-up coil head 22 enables the electronic control means to receive prescription programs and command data from the MPU or PPU; it also enables the electronic control means to handshake with the PPU or MPU and transmit utilization and system performance data. Three additional ports enable the electronic control means to monitor the fluid system: (1) a pump monitor 23 monitors actual pump actuation and hence fluid flow; (2) at least one moisture detector 24 monitors moisture within the IPIP; (3) a reservoir monitor 25 tells the chamber if the reservoir is filled or overfilled. The electronic control means also has a port allowing it to actuate an alarm means 26 which alerts the patient if a system failure or operational anomaly has occurred. (U.S. Patent Application entitled "Apparatus for detecting at least one predetermined condition and providing an informational signal in response thereto in a medication infusion system", U.S. Ser. No. 439,139, filed Nov. 4, 1982, by R. E. Fischell, describes several monitor and alert circuits which could be used—this application is incorporated herein by reference.) A final port 27 enables the electronic control means to actuate the pump solenoid 19 in accordance with a programmed prescription schedule.

Figure 3:
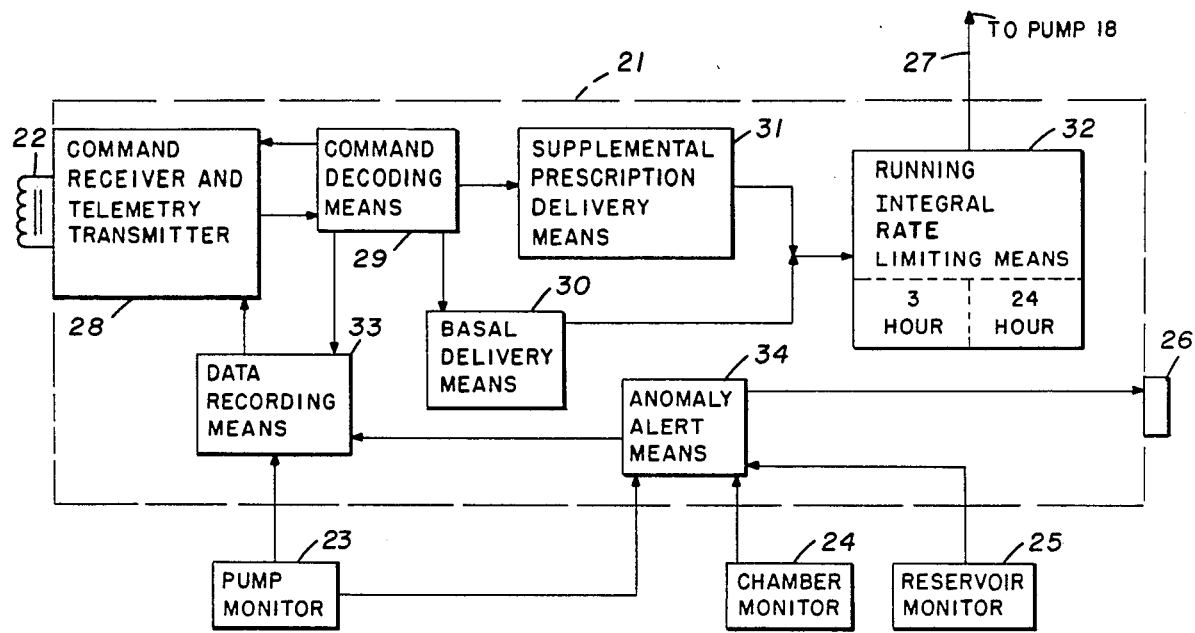
FIG. 3 illustrates a functional block diagram of the electronic control means.

FIG. 3 illustrate a simplified functional block diagram of the IPIP electronic control means 21. A command signal from the PPU or MPU is detected by a pick-up coil 22 and further processed by the command receiver and telemetry transmitter 28 producing an 8-bit code. The 8-bit code enters the command decoding means 29 which: (1) verifies that the 8-bit signal is a valid selection code; (2) verifies that the selection code is active and is appropriate for delivery (this feature assures that the patient or physician is alerted if an inadvertent operator error is made); (3) handshakes with the PPU or MPU by repeating the selection code and waiting for a valid execution code from the PPU or MPU (this feature reduces the likelihood that a spurious or interfering signal will mimick a valid prescription delivery command); (4) assigns a basal delivery schedule to the basal delivery means 30 and assigns a supplemental prescription schedule to the supplemental prescription delivery means 31; (5) stores in the IPIP memory a physician programmed basal prescription schedule and up to eight supplemental prescription schedules; and, (6) orders system utilization and performance data to be retrieved from the recording means and transmitted to the PPU.

The basal delivery means 30 is assigned a basal schedule by the command decoding means 29. The basal delivery means 30 actuates the pump in accordance with a programmed basal prescription schedule. The patient using the PPU has the option of selecting either a half or full delivery of the basal schedule.

The supplemental prescription delivery means 31 first verifies that a valid supplemental prescription schedule has been assigned. (This safety feature attempts to correct certain programming errors made by the physician.) The supplemental prescription delivery means 31 will actuate the pump in accordance with the patient's selected supplemental prescription schedule.

The running integral rate limiting means 32 is the principle safety feature contained within the electronic control means. The running integral rate limit means 32 prevents the control means from delivering a combination of basal and supplemental prescription schedules requested by the patient or physician which result in a dosage which exceeds a certain limit during a 3-hour and a 24-hour sliding window of time.

The data recording means 33 gathers utilization and system performance data which can be transmitted to the MPU. The data recording means 33 records all interactions between the IPIP and the patient controlled PPU and monitors the functioning of the fluid handling system. The data recording means 33 monitors the fluid handling system through the pump actuation monitor 23, the chamber moisture monitor 24, and the reservoir monitor 25.

An anomaly alert means 34, reviews the fluid handling system and the electronic systems performance each quarter-hour period and provides a monitor report. If two consecutive monitor reports indicate the same system malfunction, the anomaly alert means 34 actuates the alarm 26 thereby notifying the patient of a potential system malfunction.

The above functional means can be provided by a hardware electronic circuit or by a microprocessor directed by a software routine. The remainder of this application describes the preferred embodiment which uses a microprocessor directed by a software means to provide the above-described functions.

Preferred Software Controlled Embodiment

Figure 4:
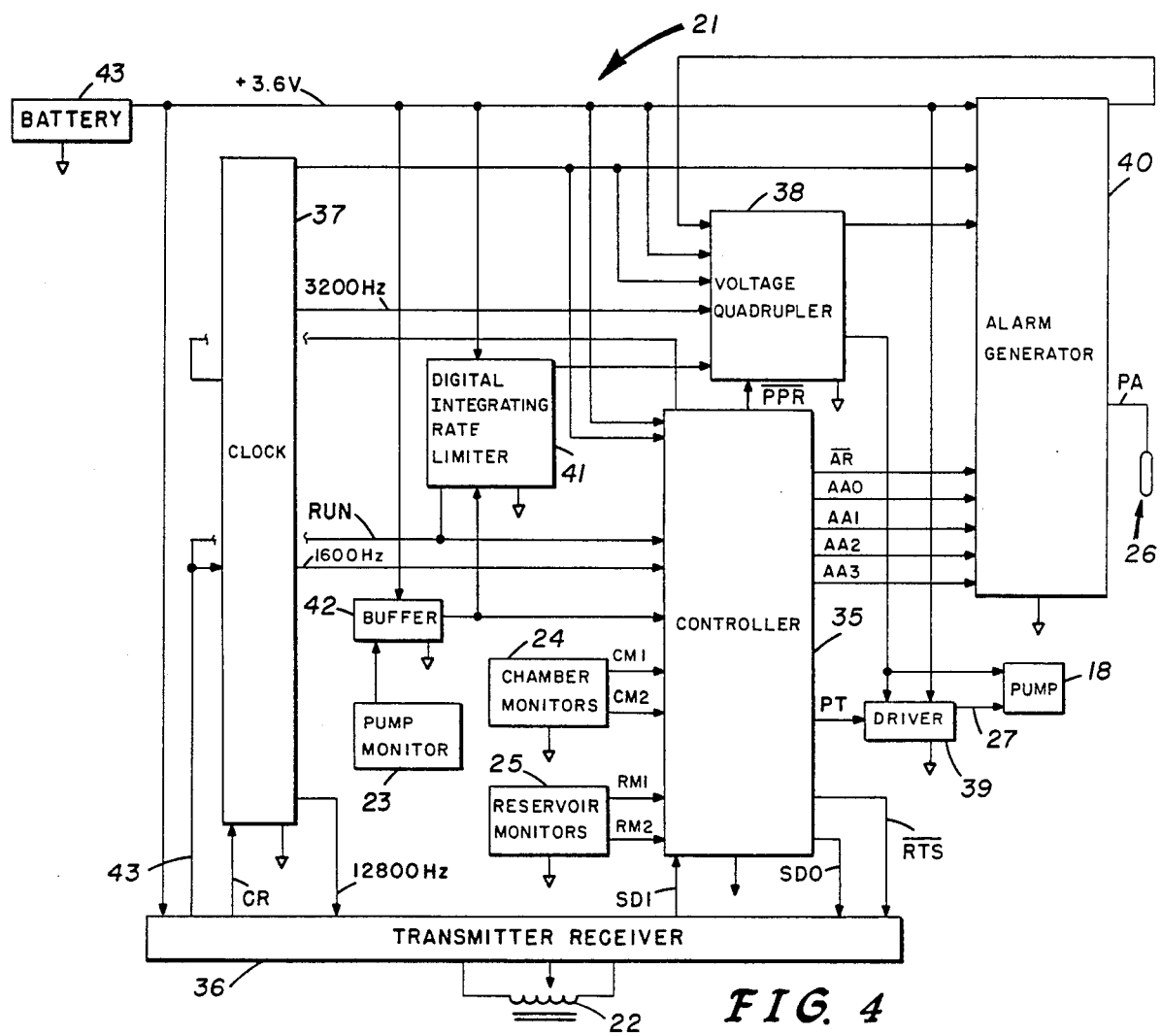
FIG. 4 is a system block diagram showing the preferred IPIP electrical control means.

FIG. 4 is an electrical system block diagram of the preferred IPIP control means 21. The diagram generally shows: a controller 35 which includes a microprocessor; a transmitter/receiver 36; a clock generating means 37; a voltage quadrupler 38; a driver circuit 39; an alarm generator 40; a digital integrating rate limiter 41; a buffer 42; and, a battery 43. The primary purpose of the control means 21, as stated previously, is to actuate pump 18. The second purpose is to actuate the alarm means 26 and thereby to alert the patient if there is a system or operator anomaly.

The driver 39 is an energy storage device (a capacitor is used in the preferred embodiment) which stores sufficient energy to actuate pump 18. The voltage quadrupler 38 steps up battery voltage and over a period of approximately 10 seconds stores sufficient energy in the driver 39 to actuate the pump 18. A pump prime request (PPR) is sent from the controller 35 which directs the voltage quadrupler 38 to charge the driver circuit 39. When sufficient energy is stored in the driver 39, the controller 35 sends the pump trigger command (PT) causing the driver to release sufficient power along line 27 to actuate pump 18.

The controller 35 also provides commands $\overline{AR}$, AA0, AA1, AA2 and AA3 which sets the alarm amplitude and actuates the alarm generator 40. The controller's alarm reques command (e,ovs/AR/) causes the voltage quadrupler 38 to provide voltage to the alarm generator 40. The alarm generator 40 then delivers the appropriate alarm signal to the alarm means 26. Controller commands AA0 through AA3 tell the alarm generator 40 what amplitude level to apply to the alarm means 26. In the preferred embodiment, the physician can program appropriate alarm amplitudes. (It will be noted that it is within the contemplation of this invention to also use an audio or any equivalent alarm means.)

The controller 35 uses the transmitter/receiver 36 to communicate with the outside world (i.e., communicate with PPU or MPU). The $\overline{RTS}$ command tells the transmitter/receiver 36 whether it is to act in the transmitter or receiver mode. The serial data output line (SDO) is used by the controller to send a serial data train to the transmitter to be transmitted to the PPU or MPU. A serial data input line (SDI) is used by the controller 35 to receive prescription data or commands sent by the PPU or MPU.

The clock generator 37 provides several timing signals: (1) a 1600 Hz timing signal provides timing for the controller's microprocessor (which is a CMOS 1802 in the preferred embodiment); (2) a 3200 Hz clock signal is generated when the communication link has been established with the PPU or MPU. A carrier recognition signal signal (CR) is sent from the transmitter/receiver 36 when a communication link is established and tells the clock generator 37 to generate the 3200 Hz clock signal. The 3200 Hz clock signal is used by the UART (see FIG. 5) which converts serial data into parallel data.

A digital integrating rate limiter 41 contains a separate timing oscillator (not shown) and an updown counter (not shown) and inhibits pump priming activity if the cumulative pump count exceeds a certain value in a certain specified time period.

A run command 43 is issued by the transmitter/receiver 36 when a selection code is received which transforms the controller from the idle to the standby state. This command will generally be sent after the IPIP has been implanted in the patient. The idle state will be discussed in detail later in this application and enables the IPIP to be stored for long periods without depleting battery capacity. In the idle state, the controller 35 is inactive and the clock generator 37 does not produce the 1600 Hz timing signal. The command to transfer from the idle to the standby state is processed by the receiver/transmitter 36 which produces the run command 43. The run command 43 turns on the 1600 Hz clock generator and resets the microprocessor and UART (see FIG. 5) contained in the controller 35.

FIG. 5 is a block diagram of the major hardware components found in the controller 35. The controller generally comprises: a microprocessor 44 (in the preferred embodiment a CMOS 1802 microprocessor is used); an 8-bit parallel data bus 45 which carries data into and out of the microprocessor 44; a read-only memory (ROM) 46 containing the fixed software instructions; a random access memory (RAM) 47 for storing the programmable prescription parameters, prescription limits, and utilization and performance data; a UART (Universal asynchronous receiver/transmitter) 48 for converting serial data received from the transmitter/receiver 36 into parallel data which can then be put on the 8-bit parallel data bus 45 or for performing the inverse operation; a multiplexer 49 which ca place identification, counter, or monitor information from the pump monitor, chamber moisture monitor, or reservoir fill monitor (see FIG. 4) on the data bus 45; an identifier number generator 50 which generates a unique code number for each IPIP; a counter 51 associated with the pump monitor, to calculate the number of times pump actuation actually occurred (this counter is reset every 15 minutes); a 4-bit register 52 which stores alarm amplitude data and a 2-bit register 53 to store the alarm request ($\overline{AR}$) and pump prime request ($\overline{PPR}$) commands.

The RAM 47 is a memory device which is used to record prescription parameters, prescription limits, control data, and utilization and performance data. The table in FIG. 6 shows the type of data stored in the controller's RAM. Each data category will be discussed as we proceed in the application. The microprocessor 44 can access this information via the 8-bit parallel bus 45. The system can use the 8-bit parallel bus 45 to retrieve data from the pump counter, reservoir monitor or chamber monitor. The controller can send a signal via the 8-bit bus 45 to registers 52 or 53 to adjust the alarm amplitude or to activate the pump. The UART 48 converts the transmitter/receiver receiver serial data format into a parallel format compatible with the requirements of the microprocessor 44. In this way the microprocessor 44 can communicate via the transmitter/receiver 36 with the MPU and PPU to receive prescription parameters and transmit utilization data.

Figure 7:
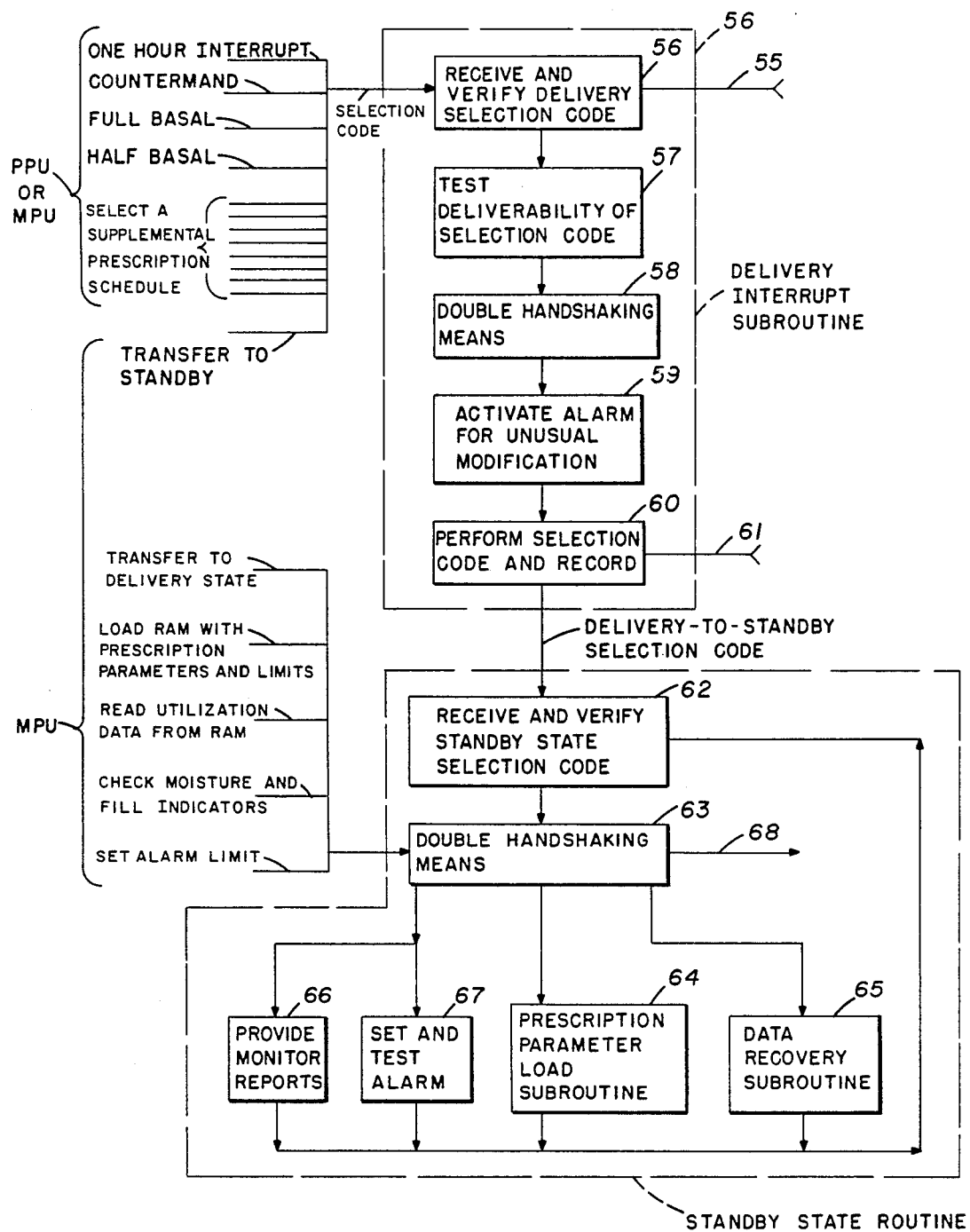
FIG. 7 is an outline of the controller's delivery interrupt routine and standby state routine.
Figure 8:
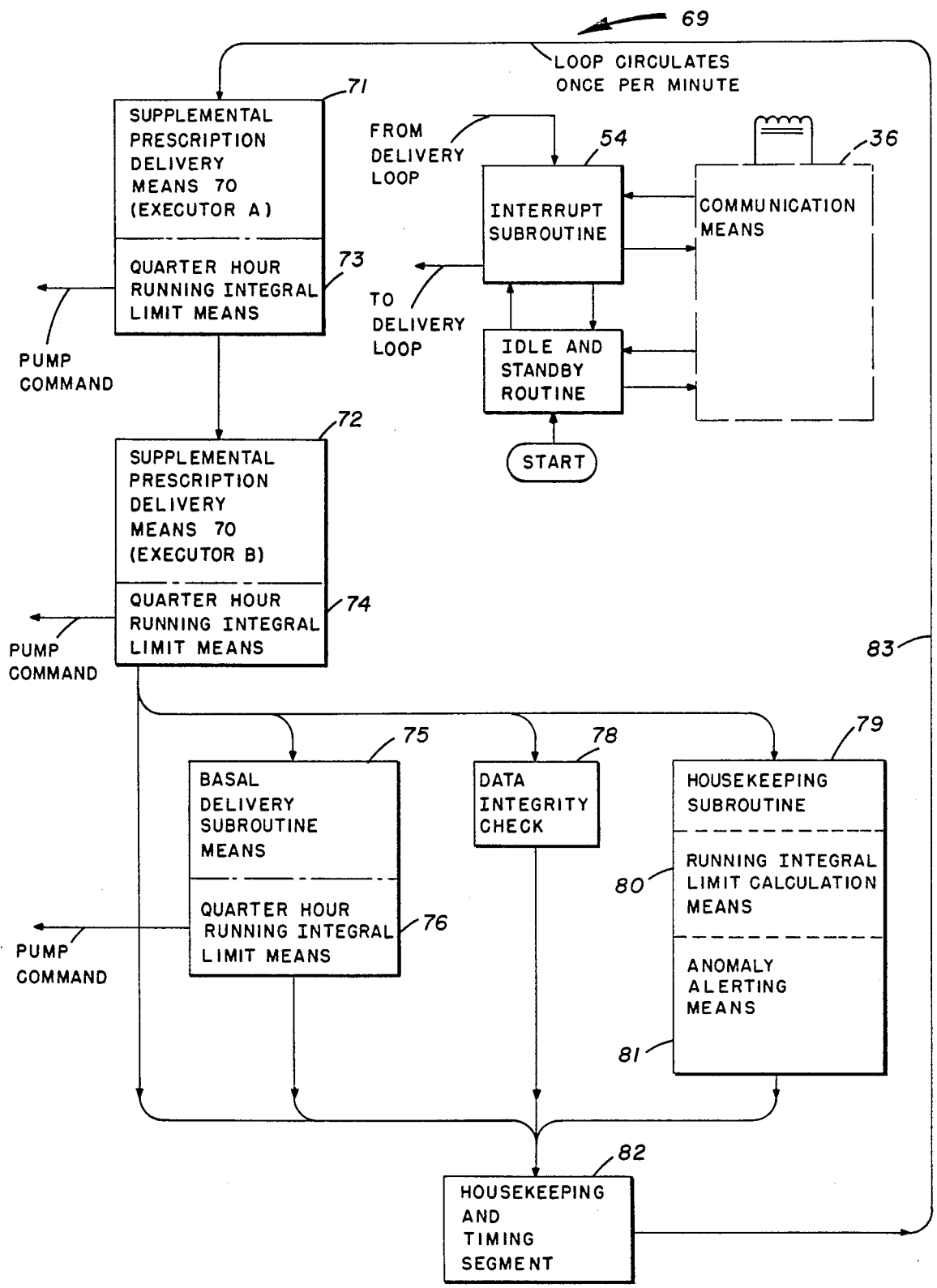
FIG. 8 is an outline of the controller's delivery routine.
Figure 9:
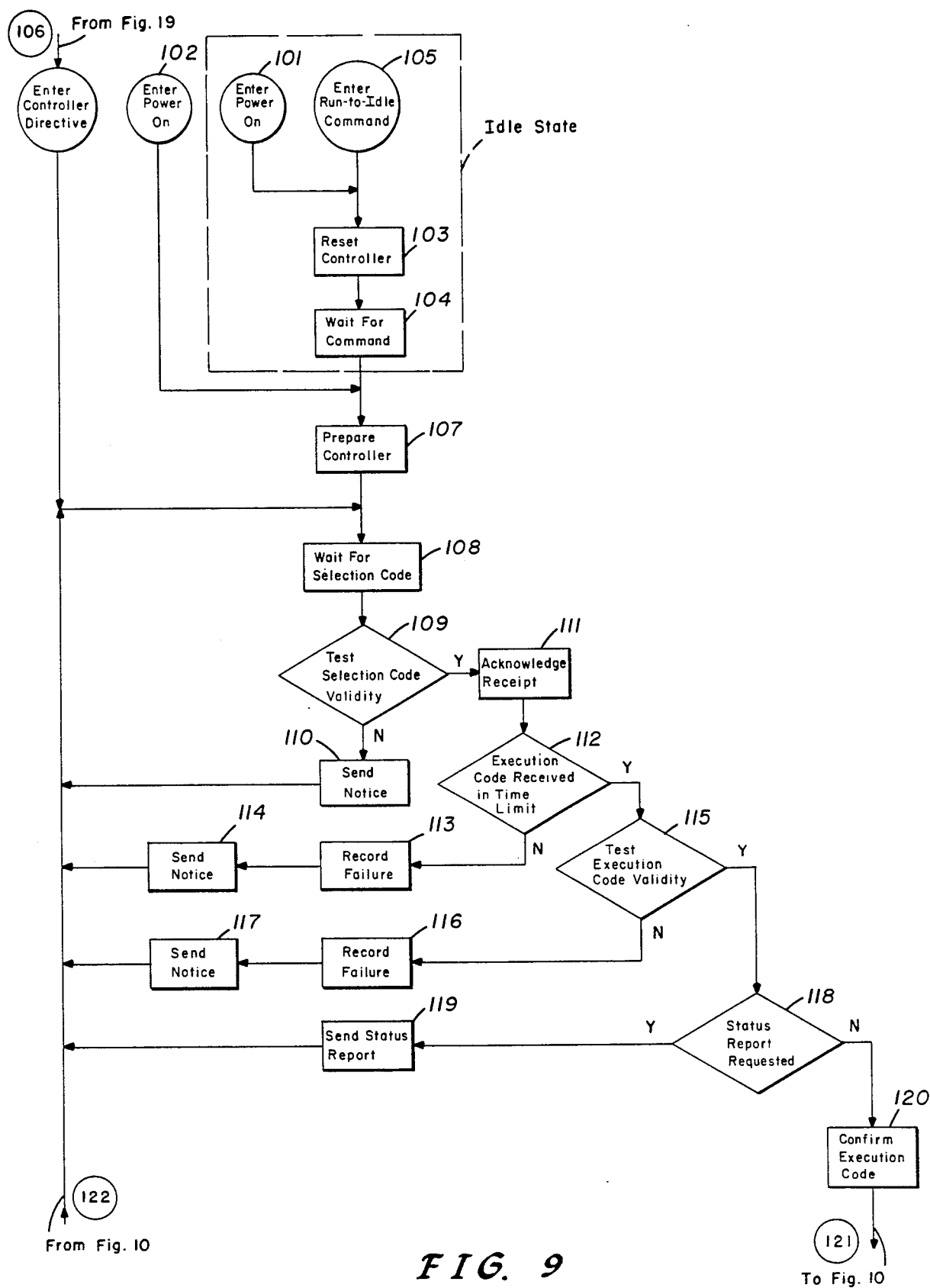
FIGS. 9 and 10 show a detailed flow chart of the idle and standby state routines.

The ROM 46 shown in FIG. 5 contains a series of fixed software instructions. These instructions enable the microprocessor 44 to actuate the pump in accordance with basal and supplemental prescription schedules, alert the patient when a system or operational anomaly is detected, record utilization data, and provide the running integral dosage limiting and other safety features needed to prevent an accidental overdose. FIGS. 7 and 8 contain a summary of the software routines and subroutines permanently fixed in ROM 46. FIGS. 9 through 20 contain a detailed flow chart describing the software stored in the ROM 46.

FUNCTIONAL OUTLINE OF SOFTWARE CONTROLLER MEANS a. Interrupt subroutine and standby routine functional summary

As mentioned previously, the preferred embodiment described in this application contains a software controlled version of the IPIP. FIG. 7 is a functional summary of the delivery interrupt subroutine and the standby state routine. These software routines enable the controller to perform as the command decoder means discussed earlier in this application and shown as block 318 in FIG. 5 of the parent case (U.S. application Ser. No. 034,155, "Implantable, Programmable Medication Infusion System", filed Apr. 27, 1979, by R. E. Fischell now U.S. Pat. No. 4,373,527). The standby state routine enables the controller to read into the RAM prescription parameters and command data and to record and transmit utilization and performance data. (In the above-referenced U.S. parent case, these functions are distributed among the following elements: 336, 334 and 320, see FIG. 5).

The delivery interrupt subroutine 54 is actuated when the receiver/transmitter conveys an 8-bit code to the UART (see FIG. 5). The interrupt subroutine exits from the delivery routine (to be discussed later) at 55 and first tests for a valid delivery selection code. The controller at block 56 tests for an 8-bit selection code corresponding to the following commands: (1) select one of the pre-programmed supplemental prescription schedules; (2) deliver the basal prescription at full or half rates; (3) countermand current directives; (4) inhibit pump actuation for a one-hour period; or, (5) transfer to the standby state.

At block 57 the controller performs various tests to determine if the selection code is active and deliverable. As mentioned previously, the physician can prohibit the patient's use of certain selection codes. One element of the prescription parameter allows the physician to deactivate certain delivery state selection codes. The controller also reviews the selection code to assess if its delivery is appropriate and/or possible.

If the selection code is valid, active and deliverable, the controller confirms receipt of the code and retransmits it back to the MPU or PPU. If the MPU or PPU verifies the selection code, it then sends an execution code to the IPIP. Unless the controller then receives a valid execution code within a specified interval, it will not carry out the mission implied by the selection code. This safety feature shown in block 58 assures that the IPIP will not be accidentally programmed by spurious or interfering signals.

The controller now asks if the selection code constitutes an unusual request. (An unusual request is one which would modify basal rate, inhibit pump operation, or countermand previous directives). If it does, the patient alarm may be activated. This safety feature shown in block 59 alerts the patient to the fact that he has made an unusual request and that he should review his intent to make that request. The controller will now at block 60 execute the selection code and assign a supplemental prescription schedule to delivery means when appropriate. The controller now returns to the delivery state at 61 unless the selection code called for transference to the standby state. (Only the MPU can transmit the selection code which requests that the controller enter the standby state.)

Once in the standby state, the controller waits at block 62 until it receives an appropriate standby state selection code. The standby state selection codes are only transmitted by the MPU and correspond to commands to: (1) transfer the controller back to the delivery state; (2) load the controller's RAM with prescription parameters and limits; (3) read utilization and performance data from the controller's RAM; (4) check the moisture and fill indicators; or, (5) exercise alarm at a specified level. The controller at block 62 verifies receipt of a valid selection code and at block 63 continues to provide double handshaking to assure that the selection code has been properly received. (i.e., once the selection code is verified, the controller retransmits it back to the PPU or MPU. The PPU or MPU verifies the code and must transmit a timely and valid execution code.)

After verification and handshaking is completed the controller, depending on the particular selection code, can branch into several subroutines. At block 64, the controller exercises a prescription parameter load subroutine (see FIG. 10) for greater detail). At block 65 the controller performs a data recovery subroutine (see FIG. 10 for greater detail). Alternatively, the controller could provide monitor reports 66, exercise the alarm, or return to the delivery state 68.

b. Delivery state subroutine functional summary

FIG. 8 is a functional summary of delivery state routine 69 which allows the controller to functionally provide the basal delivery means, the supplemental prescription delivery means, the anomaly alert means, and the 3 and 24-hour running integral dosage limit means. (In the above-mentioned U.S. parent case the supplemental prescription delivery means is performed by element 322; the basal delivery means by element 320; the anomaly detecting means by a combination of elements 318 and 328; and the 24 and 3-hour running integral dosage limits by elements 322, 326 and 324—see FIG. 5).

An excursion through the delivery state routine is completed once per minute regardless of the specific path taken around the loop. As we will discuss later, dummy delay steps are added to shorter branches so that the overall loop time is independent of path. The supplemental prescription delivery means 70 is provided by two subroutines called Executor A and Executor B (shown in greater detail in FIGS. 11 and 12 respectively). The Executor A subroutine 71 first determines if a supplemental schedule has been assigned to it for execution; if one has, it then tests the assigned supplemental prescription schedule for anomalies resulting from physician/programming error. These tests (which will be discussed in detail, later in this application) prevent an inadvertent overdose or the prolonged assignment of the executor to a non-executable schedule. If a pump actuation is appropriate, the controller will perform the quarter-hour running integral limit test means 73. This safety feature will be discussed in detail, but at this point it is sufficient to say that it prevents pump actuation if the dosage limit for a 3-hour or a 24-hour period is reached. If the limit is not reached, the controller directs the voltage quadrupler to charge the driver, thus priming the pump; the controller then triggers the driver to actuate the pump.

The Executor B subroutine 72 provides the same functions as the Executor A subroutine. Consequently, IPIP can accomplish the simultaneous execution of as many as two supplemental schedules. The Executor B subroutine also contains a quarter-hour running integral limit means 74 which prevents pump actuation if the 3-hour or 24-hour limit is reached.

Proceeding around the delivery state loop, the controller can take one of four possible branches depending on the minute count. The "minute count" specifies the number of minutes which have elapsed in the current quarter-hour period.

At the 7th minute, the controller provides the basal delivery function 75. (Shown in greater detail in FIG. 13.) The controller first determines if the PPU requests a half or full basal delivery. If the basal program calls for pump actuation, the controller again provides the quarter-hour running integral limit means 76 and determines if pump actuation would cause excessive dosage in 3 or 24-hour shifting window of time. If the limit is not reached, and if full-basal delivery mode has been established, the controller primes and triggers the pump unless pump inhibition is in effect.

At the 13th minute in the quarter-hour the controller evaluates the integrity of the prescription data stored in the RAM. This evaluation 78 will be subsequently used in formulating the monitor report and will indicate whether or not an alpha particle or transient has altered the stored prescription.

Figure 14:
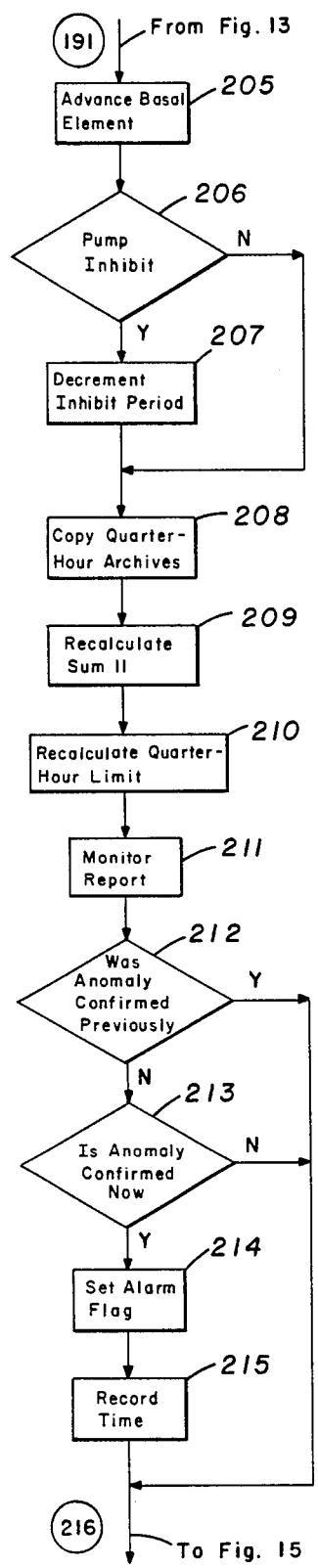
Figure 15:
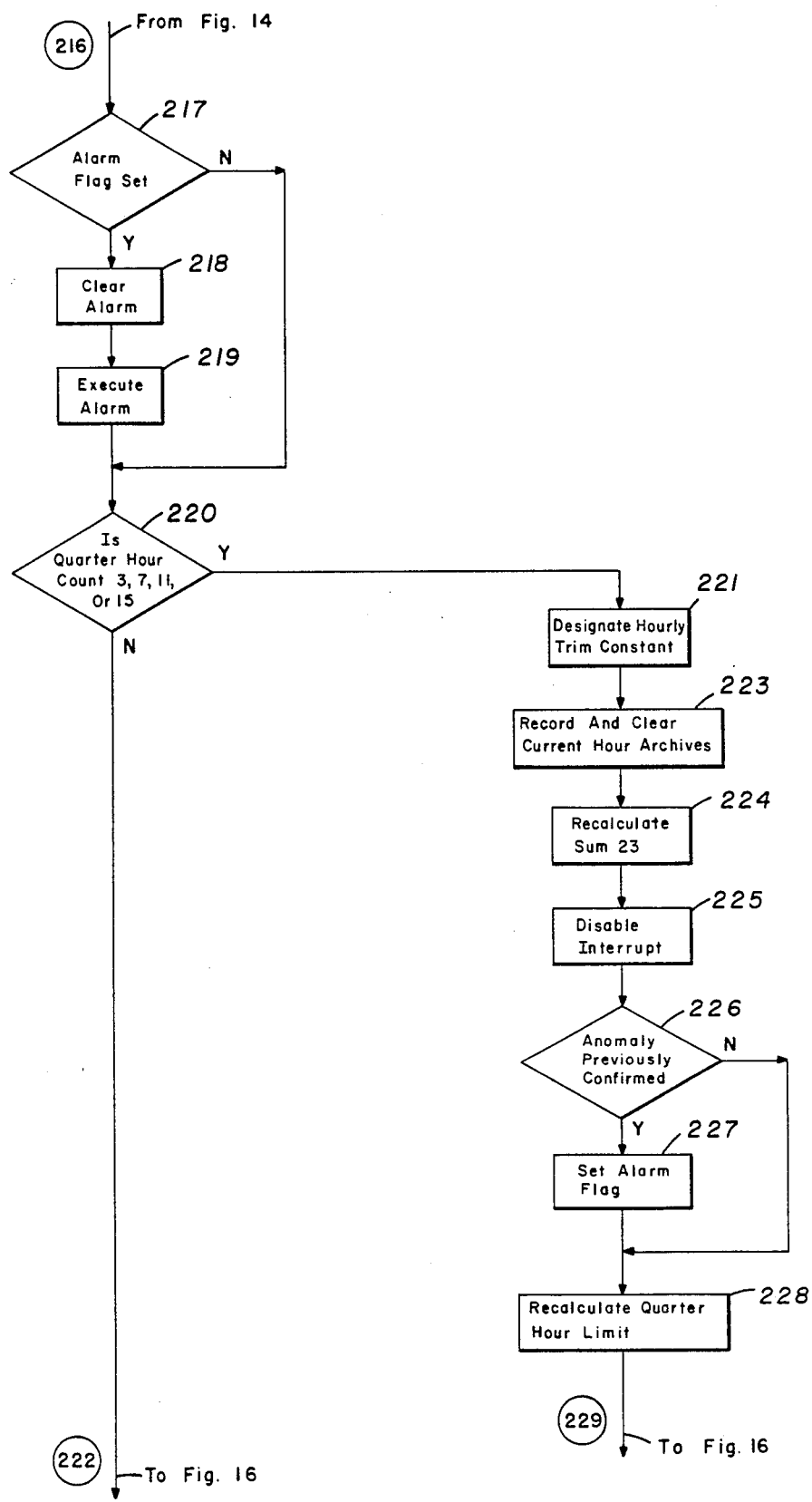
Figure 16:
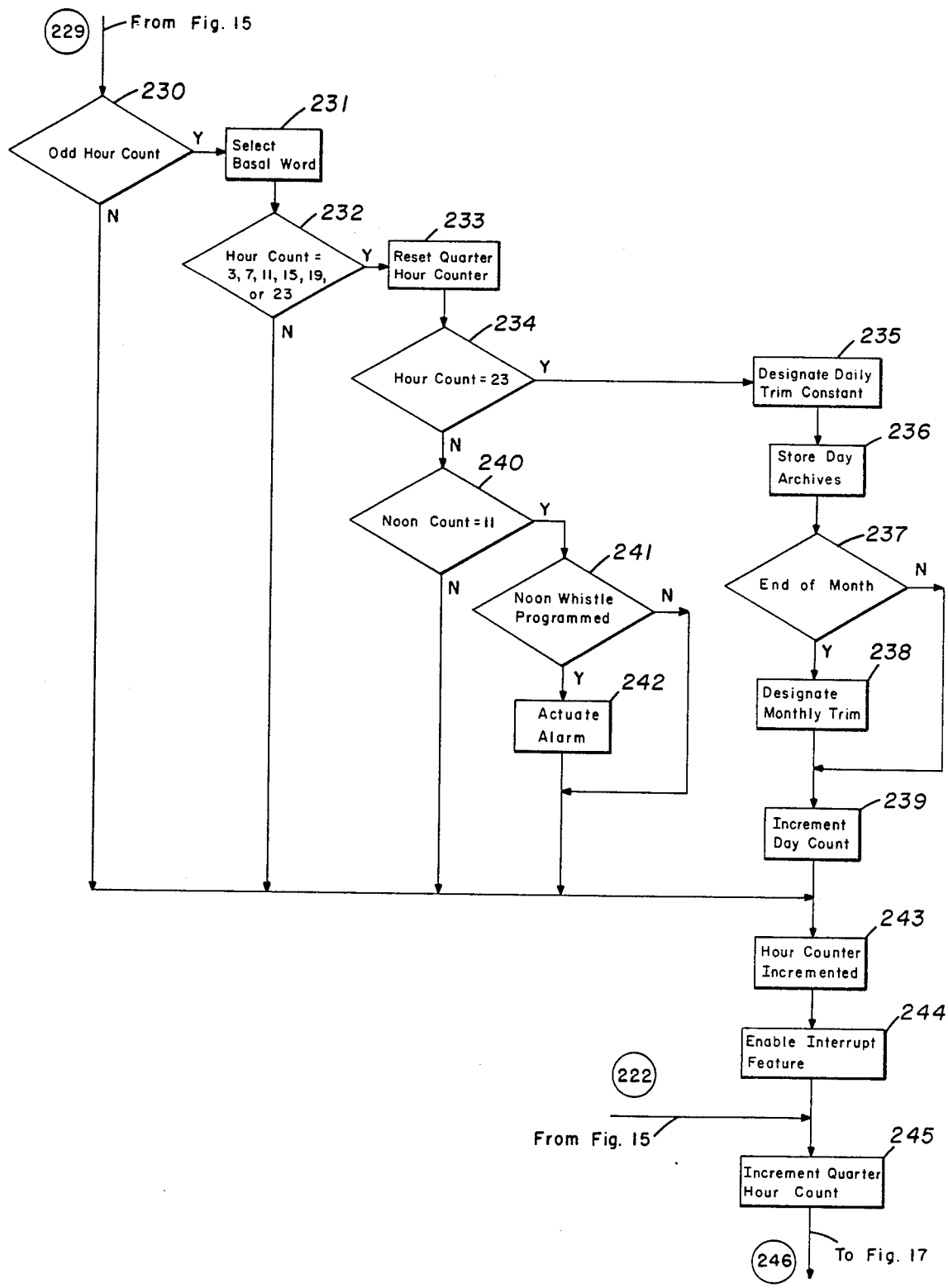
Figure 17:
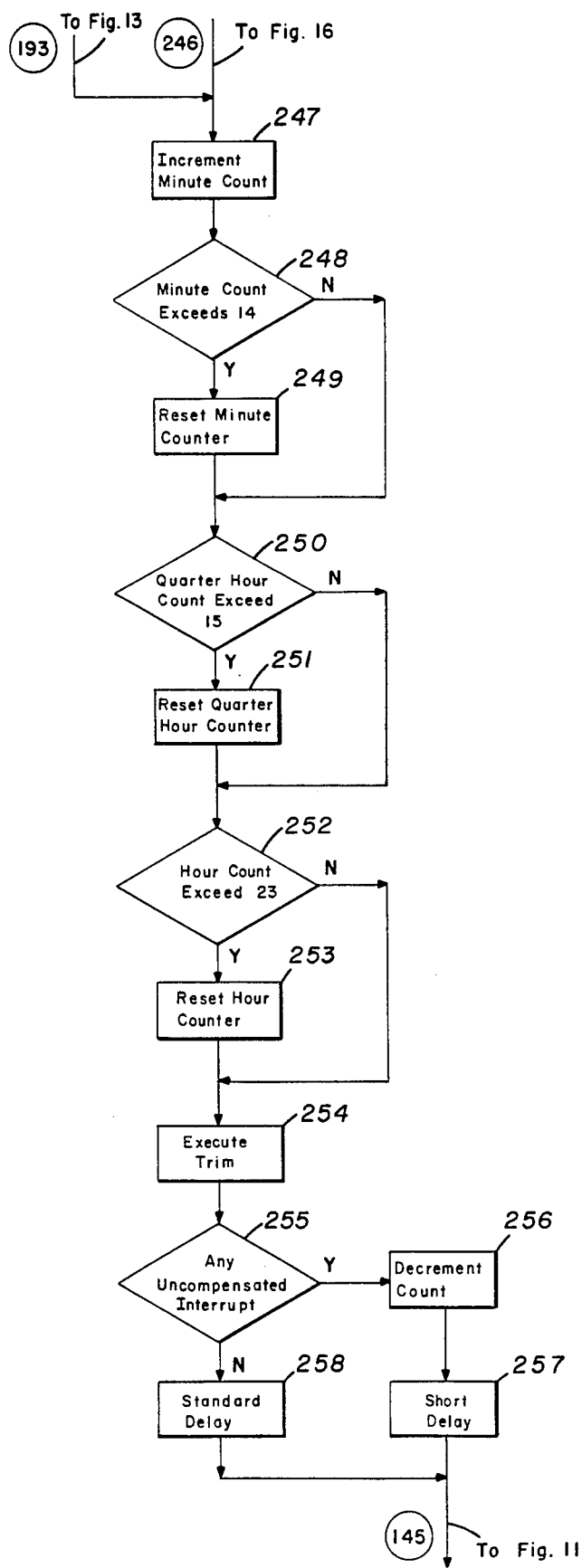

At the 14th (last) minute of the quarter-hour, the controller enters into a housekeeping subroutine 79 (shown in detail in FIGS. 14 through 16). (The housekeeping subroutine will be discussed in detail later in this application.) However, at this point it is important to point out two features provided by this subroutine. The housekeeping subroutine calculates SUM 11, SUM 23, and a quarter-hour limit which are part of the 3 and 24-hour running integral limit means 80. "SUM 11" is the number of pump actuation commands issued in the eleven preceding quarter-hours; "SUM 23" is the number of pump actuation commands issued in the twenty-three preceding hours. (The calculation of SUM 11, SUM 23 and the quarter-hour limit will be discussed in detail later in this application.) The housekeeping subroutine also provides a monitor report for spotting system malfunctions. An anomaly reporting means 81 generates a report and may alarm the patient if a system malfunction has been confirmed.

Regardless of the minute count, all the branches in the delivery state loop converge on the housekeeping and timing segment (block 82). This segment of the software increments and resets various counters and provides trimming and other timing delays. The controller has now completed one cycle through the delivery state loop 83. The controller will continue to recycle—once per minute—through the delivery state loop 83 and actuate the pump as required by the basal schedule or any assigned supplemental prescription schedules.

Idle and Standby State Routine

In the preferred embodiment the controller can operate in three states: (1) an idle state, which is used to conserve power during shipping or storage and to reset the controller; (2) a standby state during which prescription profiles and commands can be stored in the controller's RAM, or operational and other data can be read from the controller's RAM; and, (3) a delivery state during which the controller activates the pump in accordance with the basal and selected supplemental prescription profiles. When the controller is first turned on, the power-on transient will cause the controller to enter either the idle or standby state, see element 101 and 102 in FIG. 9. (The controller is turned "on" when the battery is connected to the controller and the unit is sealed).

In the idle state, the controller is reset (block 103) to establish initial conditions and then waits (block 104) to receive a command to enter the standby state (the command being processed by the transmitter/receiver 36 (see FIG. 4) and not included as part of the controller). While in the idle state, the controller circuit is dormant to conserve power and the clock pulses to the controller are suppressed. The controller can be placed in the idle state at any time during its operation by receiving a "run-to-idle" command. This entry 105 into the idle state is made by the Interrupt Subroutine which will be described in detail later in this application. The controller can be placed in a standby mode by: (1) entering 102 when the power is first turned "on"; (2) entering after receipt of a command to transfer from "idle-to-standby" 104; or, (3) enter 106 after receiving a command from the Interrupt Subroutine to enter the standby state. (The Interrupt Subroutine will be discussed in detail later in this application).

a. Controller receives and verifies standby state selection code

When the controller enters the standby state, it is first prepared at 107 and the microprocessor's registers are loaded with certain initial conditions. After the controller is initialized it waits at 108 to receive a one-byte "selection code" transmitted by the physician's MPU. The selection code is then tested (block 109) to see if it is a valid standby state selection code. If the selection code is not valid, notice is sent at (block 110) to the MPU to alert the physician that an invalid selection code was received. This feature and the other features discussed in this paragraph verifies the selection code so that an error on the part of the physician or an interfering or transient signal will not produce an invalid or inappropriate selection code. Alternatively, if a valid selection code was received, the controller acknowledges (block 111) receipt of the particular selection code by retransmitting that selection code back to the MPU via the communication means. The only 8-bit selection codes which are valid for the standby state are those which call for: (1) transfer of controller operation from the standby state to the delivery state; (2) loading of information into the controller's RAM (either in a short 6-byte format for timing purposes, or a long 384-byte format for a complete set of new prescription parameters); (3) reading of information back from the controller's RAM (either on 16-byte format which includes timing and other limited data, a 421 byte format which includes the complete set of prescription parameters, or a 1024-byte format which includes not only the complete set of prescription parameters, but all utilization data as well; (4) reporting chamber and reservoir status (i.e., moisture detectors and the reservoir fill indicators); or, (5) exercising the alarm at a specified amplitude level.

b. Double handshaking means

After the controller sends an acknowledgement command to the physician's MPU via the communications means, the MPU will send an 8-bit execution command. (The MPU first verifies that the selection code that it received from the IPIP was the selection code it had previously transmitted.) The MPU must then send the 8-bit execution code within a certain prescribed time period in order to initiate the action specified by the preceding selection code. The controller (block 112) tests to see if the execution code was received within the prescribed time limit. If the execution code was not received within the time limit, the failure is recorded in the Controller's RAM at block 113 and appropriate notice is sent (block 114) to the MPU indicating that the execution code was not timely received. If, however, the execution code was timely received, the execution signal is now tested at block 115 to see if it is valid. (i.e., to see if the execution signal has the correct 8-bit code.) If the execution code is not valid, the failure is recorded (block 116) and notice of such failure is sent (block 117) to the MPU. As mentioned earlier, the above handshaking is a critical safety feature for an interactive infusion system in which both the physician and patient can influence medication delivery patterns.

c. Controller provides status report

If the execution code is valid and received within the prescribed time limit, the program advances to block 118. At block 118 the controller asks whether the selection code requests a status report (i.e., a report indicating whether there is moisture in the electronics or freon chambers, or whether the reservoir is full, or overfilled). If a status report is requested, the controller will at (block 119) activate the communication means and transmit that status to the MPU. If a status report was not requested, the controller responds by transmitting to the MPU a confirmation code which is identical to the execution code (block 120).

d. Controller sets alarm controls

Figure 10:
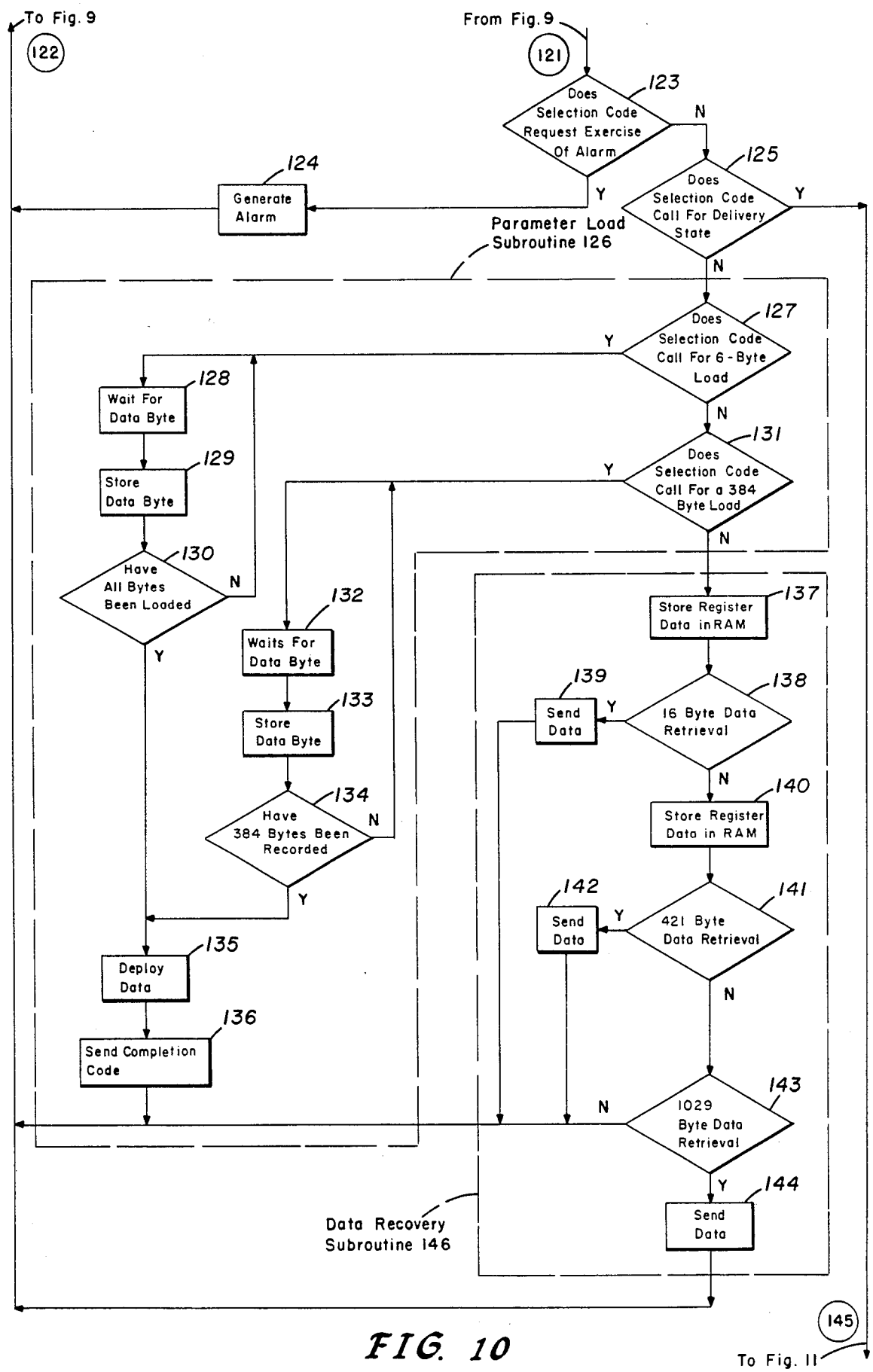

Turning to FIG. 10, we continue to block 123 which determines whether the selection code requests an exercise of the IPIP alarm means. If the selection code requests that the alarm be exercised, the controller proceeds to block 124 and energizes the alarm at the specified amplitude. If, however, the selection code does not request an alarm actuation, we proceed to block 125 which asks whether the selection code constitutes a request to transfer the controller to the delivery state. (As mentioned previously, in the delivery state the controller will actuate the pump means in accordance with the basal and supplemental prescription profiles selected from the controller's RAM.) If the selection code calls for a transfer to the delivery state, we exit from the standby state routine at 145; if not, we proceed to the prescription parameter load subroutine 126.

e. Prescription parameter load subroutine

The prescription parameter load subroutine 126 allows the physician to record in the controller's RAM up to eight supplemental and one basal prescription schedule, set prescription and control limits, and record timing data. If the selection code calls at block 127 for 6-bytes of data to be loaded, the controller waits (block 128) for the first data byte to be received and then stores (block 129) that data byte into the controller's RAM. At block 130 we count the number of data bytes received from the MPU and exit the data gathering loop when all six bytes have been received and stored. As specified previously, the 6-byte load contains timing information which allows the IPIP schedule to be coordinated with the actual day cycle. If, however, the selection code does not request a 6-byte data load, we proceed to determine at block 131 if the selection code constitutes a request to load 384 bytes into the controller's RAM. As mentioned previously, the 384-byte load contains prescription profile and control information. If such a load is requested the controller again waits at block 132 until a data byte is transmitted by the MPU and stores at block 133 that data byte in the controller's RAM. The data gathering loop continues at block 134 until all 384 bytes have been received and recorded. When the data bytes have been recorded we proceed to deploy at block 135 certain bytes of the data in the microprocessor registers and transmit at block 136 a completion code to the MPU to alert the physician that the new time data, and prescription parameters have been stored in the controller's RAM.

f. Data recovery subroutine

If the selection code does not require data to be stored in the controller's RAM we enter the data recovery subroutine 146 which requires the controller to read data from its RAM and transmit such data to the MPU. At block 137 the controller is directed to retrieve selected data from the microprocessor registers and store that data in RAM. The controller then determines at 138 if the selection code requests the transmittal of 16 bytes (these are the bytes relating to IPIP timing) and if so the controller will select and transmit at block 139 the 16 bytes via the communication means. If, however, prescription profile and control data is to be retrieved (block 141 in FIG. 10) we store (block 140) additional register data into the RAM and send at block 142 the 421 bytes to the MPU. If, however, the selection code is tested at 143 and requests a dump of the entire RAM (1029 bytes) the data is collected and transmitted at block 144 to the MPU. The 1029-byte dump of the RAM not only contains the prescription profile and control data, but pump and control system operational history. After the prescription parameters and operational history is retrieved and transmitted (at blocks 139, 142 or 144) the controller returns to block 108 (FIG. 9) via path 122 to wait for another standby selection code to be sent by the physician.

In operation, the physician first establishes a communication interface between the IPIP and the MPU. The physician will order the IPIP to enter the standby state. Generally, the physician will first send the selection code which requests a dump of all data residing in the controller's RAM. The physician can display this data on the MPU screen and confirm the device identity by its unique identification code. The physician can analyse the previous prescription parameters, the prescription limits and the IPIP system operational history. The evaluation data contained in the 1029 byte RAM dump generally indicates: (1) cumulative pump counts; (2) daily pump counts; (3) hourly pump counts; (4) supplemental schedule invocation counts; (5) inhibit counts; (6) limit counts; (7) countermand counts; (8) basal half rate counts; (9) elapsed time; and, (10) final epoch. In addition, the physician is provided the following performance data: (1) first confirmed anomalous monitor report; (2) current monitor report; (3) time of first confirmed anomalous monitor report; (4) current chamber and reservoir status; (5) number of disacknowledged commands; and, (6) number of disconfirmed commands. The physician could now specify new prescription parameters or control limits. The MPU would send the selection code for the prescription parameter load subroutine and would then transmit the following parameters: (1) basal prescription profile; (2) up to 8 supplemental prescription profiles; (3) limits on patient's use of the PPU (generally without such limits the patient can use the PPU to reduce the basal profile by one half, to select any two of the stored supplemental prescription profiles for simultaneous delivery, inhibit pump actuation for onehour periods or countermand previous selections); (4) set the 3-hour running integral dose limit; (5) set the 24-hour running integer dose limit; (6) set the cumulative dose limit; (7) set the alarm criteria (it is possible to inhibit the alarm operation for certain conditions); (8) set alarm amplitude; (9) set clock trim constants; and, (10) initial epoch. After the new prescription parameters are stored in the controller's RAM, the physician could send another selection code and display the prescription parameters and control limits that were actually stored in the controller's RAM to assure that the prescription has been correctly received and stored by the controller. After the new prescription parameters are verified, the physician can transmit the selection code which transfers the controller from the standby to the delivery state at the initial epoch embodied in the new prescription. After the operation is completed, the communication link can be disestablished and the controller will proceed in the delivery state to activate the pump means as required by the basal and selected supplemental prescription schedules.

Delivery State Routine

The flow chart for the delivery state is shown in FIGS. 11 through 17. The delivery flow chart comprises a loop containing several logical branches and is traversed once per minute. The time to traverse the delivery state loop is the same no matter which of the loop's logical branches are included in a particular excursion. To accomplish this, the software introduces delays which are not shown explicitly on the flow chart. This technique (adding delay) is well known in the art. The programmer merely adds the required number of delay steps in particular logical branches so that no matter what route one takes through the delivery state loop, the elapsed time will be one minute. This technique is also used in the Standby Routine and the Interrupt Subroutine, as well as all subroutines embodied in these routines. Alternatively, one could implement the program by using a clock-driven interrupt scheme which would initiate excursions through the loop at one-minute intervals. Either embodiment will work satisfactorily; however, the first method was chosen because it requires fewer hardware components.

The controller enters the delivery state at 145, after receiving a command from the MPU to enter the delivery state. Block 147 sets the nominal trim constant and prepares the controller for delivery activities. The nominal trim constant, which will be discussed in detail later in this application, is preset so that over a long period of time the delivery state loop is recycled once a minute.

a. Supplemental prescription delivery means

Figure 11:
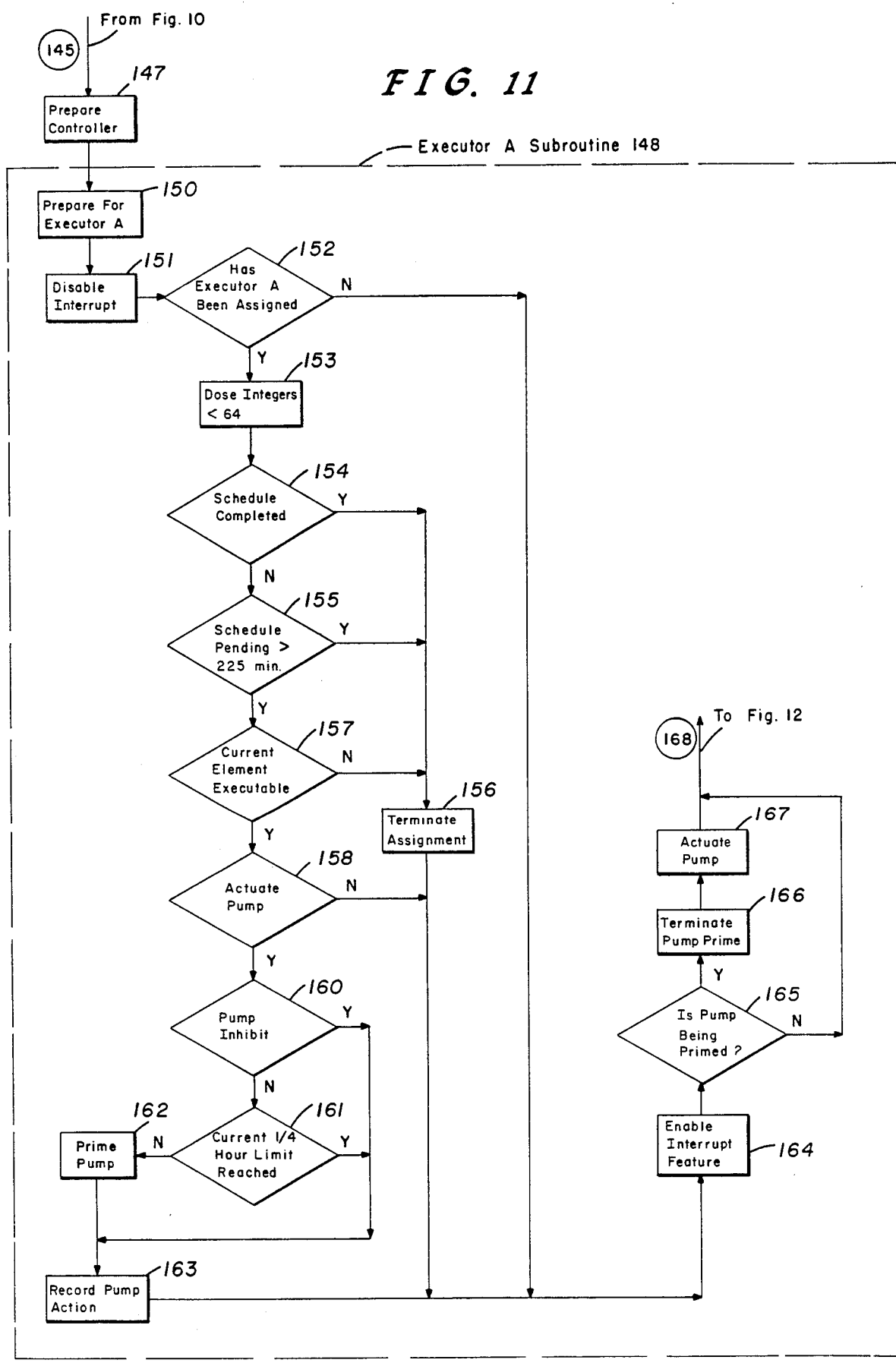
FIGS. 11 through 17 show a detailed flow chart of the delivery routine with FIGS. 11 and 12 showing the supplemental delivery means, FIG. 13 showing the basal delivery means, FIGS. 14 through 16 showing the housekeeping subroutine, and FIG. 17 showing an additional housekeeping segment.
Figure 12:
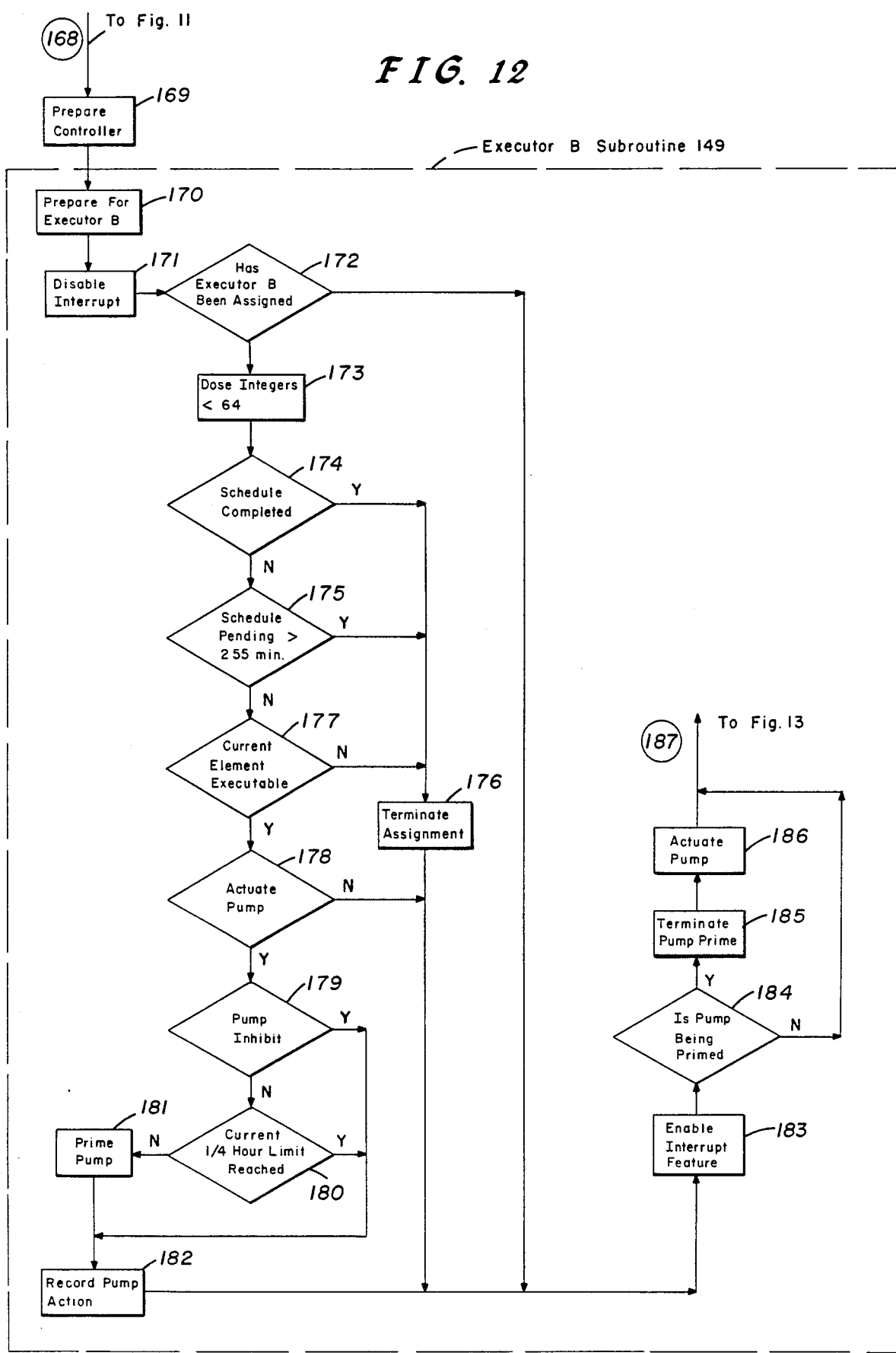

The software for the preferred embodiment has two subroutines which are capable of delivering supplemental prescription schedules. These software subroutines are shown in FIG. 11 and 12, respectively, as Executor A (subroutine 148) and Executor B (subroutine 149). Executor A is encountered first as we proceed around the delivery state loop. The software first sets (block 150) the microprocessor variables associated with Executor A and then disables (block 151) the interrupt feature. (The interrupt feature is a separate subroutine which allows a physician or patient to interrupt the delivery state so that certain requests for modification of drug delivery can be introduced, or so that the controller can be transferred into the standby state.)

At block 152 the controller determines if Executor A has been assigned a supplemental prescription schedule. If no assignment has been made, the controller bypasses the pump actuation segment of Executor A. If, however, a supplemental scheduled has been assigned, we proceed to determine whether the supplemental dosage is within prescribed limits.

It is important at this point to describe the supplemental prescription schedule used in the preferred embodiment. The supplemental prescription schedule is a sequence of integers, each integer corresponds to a minute count—that is, the number of minutes of elapsed time since the particular supplemental prescription schedule had been assigned to one of the Executor subroutines. A particular supplemental prescription profile can at most request one pump actuation per minute. The following is an example of a supplemental prescription schedule:

1, 3, 4, 5, 7, 15, 40, 70

Using the above example, Executor A would cause the pump means to actuate once at the 1-minute count, once at the 3-minute count; once at the 4-minute count, etc. The maximum number of integers associated with the supplemental prescription schedule cannot exceed 64. In other words, not more than 64 pump actuations can be incorporated in a single schedule. Since each integer corresponds to a time subsequent to that of the previous integer, each integer in the sequence must be greater than the previous integer. Also, the supplemental prescription schedule used by the preferred embodiment is designed to span 255 minutes or less. In other words, the supplemental prescription schedule is limited to deliver 64 pump actuations or less in a time frame of 255 minutes or less.

Returning to the flow chart at block 153 (FIG. 11) the controller asks whether the total dosage in the supplemental prescription schedule exceeds 64 pump actuations. This feature assures that IPIP will not actuate the pump more than 64 times in executing a single supplemental schedule, even if that schedule (erroneously) calls for a greater number. This safety feature allows the IPIP controller to override one type of error which might otherwise have detrimental effect on the patient.

Proceeding to block 154 the controller determines whether the total dosage requested by the particular supplemental prescription schedule has already been delivered on a prior excursion through Executor A. If delivery is complete, the subroutine bypasses pump actuation and the assignment is terminated at block 156. If not, the controller proceeds to block 155 to determine if Executor A has been assigned a particular supplemental prescription schedule for more than 255 minutes. If so, it means there is an unallowed supplemental prescription schedule and the supplemental prescription schedule assignment is therefore terminated at block 156. Block 155 is a safety feature preventing Executor A from getting locked indefinitely in an improper supplemental prescription schedule.

Proceeding to block 157 the controller determines if the current integer in the assigned supplemental prescription schedule is executable. If the current integer in the supplemental prescription schedule is smaller than the minute count, the program would get locked into an endless loop. For example, if the physician erroneously programmed the following sequence: 1, 2, 3, 2, Executor A could not proceed past integer 3 and would in essence be frozen in a continuous loop. To protect the controller from getting locked in such a continuous loop block 157 identifies an unexecutable schedule and directs the controller to proceed to block 156 where the improper supplemental prescription schedule assignment is terminated.

We have now established that a proper supplemental prescription schedule has been assigned to Executor A. Proceeding to block 158 the controller determines if the current integer element in the supplemental prescription schedule calls for pump actuation (i.e., Does the integer equal the minute count—The minute count is determined by a counter which will be discussed later). If actuation is indicated, the controller at block 160 determines if pump inhibition is in effect. (Pump inhibition is a selection made by the patient's PPU which allows the patient to inhibit medication delivery for up to eight, one-hour periods. This safety feature allows the patient to terminate pump activity if he believes that he would otherwise receive undesired medication.)

We now encounter the first segment of the 3-hour and 24-hour integral rate limiting software means. Proceeding to block 161 the controller determines whether the current quarter-hour limit has been reached. Although the quarter-hour running integral limit is calculated elsewhere in the delivery state loop, it is important to briefly explain what the quarter-hour limit calculation involves. The quarter-hour limit is calculated in a housekeeping subroutine which is enabled once in each quarter-hour period. The controller sums the number of pump actuations which have occurred in the last eleven quarter-hour periods (called SUM 11) and in the last twenty-three hour periods (called SUM 23). These quantities are compared respectively to the 3-hour running integral dosage limit and 24-hour running integral dosage limits. The quarter-hour limit is the smaller of [(3-hour limit)—(SUM 11)] and [(24-hour limit)—(SUM 23)].

At block 161, the controller determines the number of pump actuations which have occurred during the current quarter-hour period. If this number equals or exceeds the quarter-hour limit pump actuation will not occur. Since the quarter-hour limit is recalculated every quarter-hour, the effect is to produce a running integral dosage limit which has a sliding 3-hour and 24-hour time window.

If the quarter-hour running integral limit is reached, the program at block 161 bypasses pump priming and in this way the software routine prevents medication from being delivered at inappropriate levels during the shifting time windows.

If the quarter-hour running integral limit is not reached, the controller proceeds at block 162 to prime the pump. In the preferred embodiment a capacitor is first charged for approximately 10 to 15 second to the required energy level—this is called pump priming. Later in the flow chart, we will see that the capacitor is discharged through the pump solenoid, thereby causing pump actuation. Proceeding to block 163, the controller records whether: (1) the pump will be actuated; (2) the pump actuation was inhibited because the quarter-hour limit was reached; or, (3) the pump actuation was inhibited because the patient called for pump inhibition. This data is stored in the controller's RAM.

We now proceed to actuate the pump. At block 164 the interrupt feature which was disabled at block 151 is re-enabled. Proceeding to block 165 the controller asks if the pump is being primed. At block 166 the controller terminates pump priming activities and at block 167 the pulsatile pump is actuated by connecting the charged capacitor to the pump solenoid. The Executor A subroutine is now completed for this cycle through the delivery state loop.

FIG. 12 shows the Executor B subroutine 149. We enter Executor B at 168 after leaving the Executor A subroutine. The patient's PPU can select a supplemental prescription profile to be delivered by Executor B. Actually, the first supplemental prescription schedule, if any, chosen by the patient will be assigned to Executor A and the second supplemental prescription schedule, if any, chosen by the patient will be assigned to Executor B. The Interrupt Subroutine discussed later in this application, performs this assignment. The flow chart for Executor B is identical in function to the flow chart for Executor A, therefore, further description is not necessary.

b. Branching segment of delivery state routine

This segment of the delivery state routine 188, 189, and 190, causes the controller to select between four possible branches, depending on the minute count. One possible branch contains the basal delivery subroutine; a second branch contains a subroutine which checks the controller's RAM for data integrity; a third branch contains a housekeeping routine which is engaged every quarter hour; and, the last branch bypasses directly to another housekeeping segment which is performed every cycle through the delivery state loop.

At this point, in the delivery state loop, the controller has used up approximately 32 seconds. Continuing along the delivery state loop, the controller branches into four possible paths depending on the "minute count" (see blocks 188, 189, 190 in FIG. 13). The "minute count" is an integer which is advanced each time the delivery state loop is completed and is reset every quarter hour (e.g., the "minute count" in the preferred embodiment ranges from 0 to 14). During a quarter hour period, the delivery state routine must, in addition to delivering the required supplemental prescription schedules, deliver the prescribed basal dosage, recalculate the quarter hour running integral limit, and perform various housekeeping and timing functions. In order to accomplish these various tasks and not exceed the one-minute loop time, the software routine assigns various tasks to different minute counts encountered during a quarter hour period.

Figure 13:
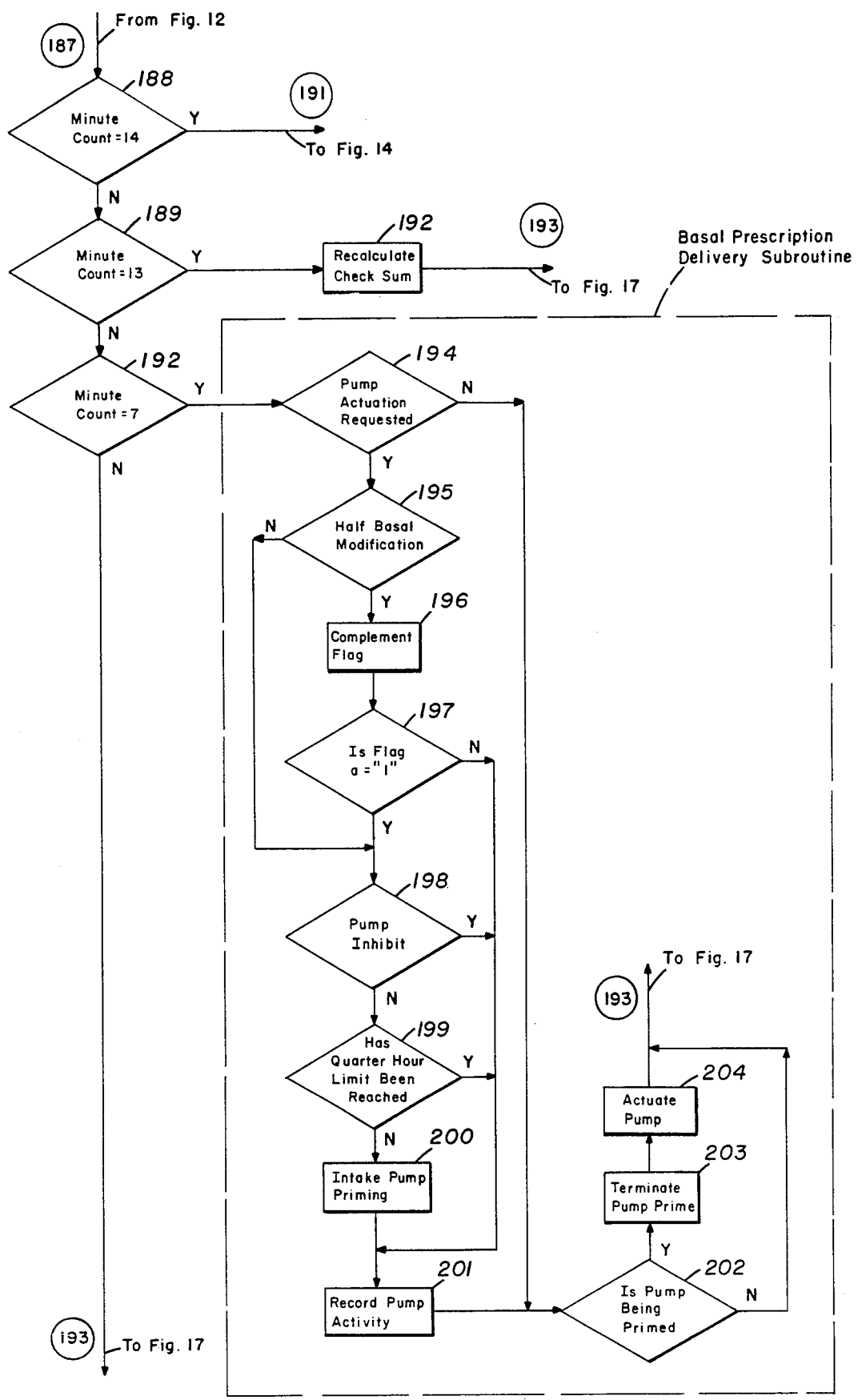

Returning now to blocks 188, 189 and 190 in FIG. 13, we see that if the "minute count" is 14 we branch at 191 to a housekeeping subroutine which recalculates a quarter hour running integral limit and performs various housekeeping and timing functions. If, however, the minute count is 13 we branch to a subroutine (block 192) which recalculates CHECKSUM, which will be used subsequently to determine if the prescription parameters stored in the controller's RAM have been inadvertently altered. CHECKSUM is a number obtained by adding those bytes stored in the controller's RAM which represent the prescription parameters. The prescription parameters in the RAM are considered to be 8-bit numbers and the CHECKSUM is an 8-bit answer obtained by adding the various 8-bit numbers contained in the prescription data and disregarding the carry. If any one of the prescription parameter bits are changed it will result in a different 8-bit CHECKSUM number. The CHECKSUM number is used later in the delivery state loop at block 211 (FIG. 14) when the controller is asked to provide a monitor report (the monitor report will be discussed in detail later in this application).

Returning to block 190, the controller asks if the "minute count" is 7, and if so we branch to the subroutine which administers the basal prescription; if not, we continue at 193 to another subroutine which provides housekeeping once each cycle through the delivery state loop. It should be noted that the "minute count" designated for each of the above tasks is arbitrary, and that the only limitation in the preferred embodiment is that each of the above tasks be completed within a quarter hour period. Other software embodiments are envisioned which branch at different "minute counts" or lump different functions in different branches of the delivery state loop.

Basal Prescription Delivery Subroutine

The basal prescription delivery subroutine as shown in FIG. 13, directs the controller to activate the pump in accordance with the physician's programmed basal prescription schedule. The controller runs through the basal prescription subroutine once every quarter hour period. In the preferred embodiment the controller branches into the basal prescription delivery subroutine at the 7th minute of the quarter hour. The controller proceeds at block 194 to ask if the current element of the basal prescription schedule calls for pump actuation. The controller looks at a particular bit in the basal prescription schedule and if that bit is a "1" the controller continues into the basal prescription subroutine to further determine if any other command or limitation will inhibit pump actuation.

In the preferred embodiment the basal prescription schedule contains a sequence of 96 bits which are programmed by the physician. (NOTE: The patient's PPU does not have the capability to modify the basal prescription schedule; however, the PPU can be used to select a half or full-basal rate delivery. The half basal delivery rate simply calls for pump actuation for every alternate "1" in the full basal prescription as programmed by the physician.) Each bit in the basal prescription corresponds to a particular quarter-hour among the 96 quarter-hour periods which span the daily cycle. Therefore, "1" appearing in the basal prescription directs the controller to actuate the pump during that particular quarter-hour. Although in the preferred embodiment, each bit in the basal sequence is associated with a particular quarter-hour period, it is within the contemplation of the invention to generate a software embodiment in which the interval associated with each bit of the basal schedule may be less than or greater than a quarter hour.

The controller now enters the segment of the basal prescription delivery subroutine which asks if the half basal or inhibit commands are in effect. Returning to the flow chart (FIG. 13), the controller was asked to determine at block 194 if the current element of the basal prescription schedule called for pump actuation. If the current element bit is "1" the controller proceeds to block 195 and asks if the half basal directive is in effect. If the half basal directive is not in effect we proceed to block 198; if, however, it is in effect, we proceed to block 196 where the controller complements a one-bit half basal control flag. Proceeding to block 197, the controller asks if the complemented element is "1". If the element is not a "1" we branch around the pump priming activity; if, however, it is a "1" we proceed to block 198. At block 198 the controller asks if pump inhibition is in effect. As mentioned previously, the patient, using the PPU, can inhibit pump actuation for a certain number of one-hour periods.

The controller now proceeds to the segment of the basal prescription delivery subroutine which determines if the current basal dosage will exceed the 3-hour or 24-hour running integral prescription limit by comparing a quarter-hour dosage count with the quarter hour limit. If the inhibit is not in effect, the controller proceeds to block 199 and determines if the quarter hour running integral limit has been exceeded. The quarter hour running integral limit means is contained in block 199 and operates in a similar manner to blocks 161 and 180 found in Executors A and B. If a pump actuation cycle would result in a pump count for the current quarter hour which equals the quarter hour limit, the controller branches to block 201 and avoids pump priming. If, however, the quarter-hour limit is not reached, the controller proceeds to block 200 and initiates pump priming.

The next segment of the basal prescription delivery subroutine is used to actuate the pump and to record pump utilization history. Proceeding to block 201, the controller records the deposition of the scheduled pump activity. That is, the controller records, (1) whether the pump is being primed; (2) whether pump actuation was inhibited by an inhibit command; (3) whether the quarter-hour running integral limit was exceeded; or, (4) whether the half-basal modification prevented pump actuation. Proceeding to block 202 we ask if the pump is being primed. If the pump is being primed we terminate priming at 203 and actuate the pump means at 204. After pump actuation at block 204 the controller proceeds to block 247 (see FIG. 17). If, however, the pump was not being primed we also proceed to block 247, (FIG. 17) and bypass pump actuation. Block 247 will be discussed in detail later in this application and provides various housekeeping acitivities before the controller recyles through the delivery stat loop.

Housekeeping subroutine and running integral limit calculation and an anomaly alerting means FIGS. 14 through 16, show the flow chart for the housekeeping subroutine used to calculate the quarter-hour limit and provide other housekeeping functions. In the preferred embodiment, the delivery state program branches to this subroutine at the last minute of the quarter hour (see block 188, FIG. 13). In FIG. 14 the controller first proceeds to block 205 and advances the basal schedule element selector. In this step the controller identifies the next bit of data stored in the basal prescription profile. This identification is utilized in executing the basal schedule during the next succeeding quarter-hour period. At 206 the controller checks to determine if pump inhibition is in effect. As mentioned previously, the patient can suspend pump operation for a certain number of 1-hour intervals. (NOTE: blocks 160, 179, and 198, in FIGS. 11, 12, and 13 respectively, suspend pump actuation in the Executor and basal subroutines when pump inhibition is in effect). If the pump inhibition is in effect, the controller proceeds to block 207 and decrements the inhibited quarter-hour count by one. (The one-hour inhibition period corresponds to four quarter-hour periods.) When the inhibited quarter-hour count has been reduced to zero, the pump can again be actuated as directed by the delivery routine.

The next segment of the housekeeping subroutine recalculates the quarter-hour limit. Proceeding to blocks 208, 209 and 210, the controller recalculates the quarter-hour dosage limit. At 208 the controller copies certain data stored in the quarter hour archives (e.g., the number of pump actuation commands, the number of actual pump actuations, and other such measurements which were recorded in the controller's registers during the present quarter-hour period) and stores them in more permanent memory archives in the RAM. At 209 the controller recalculates SUM 11 which is the number of pump actuation commands issued in the immediately preceeding eleven quarter-hour periods. The controller retrieves from RAM archives pump actuation counts for each of the proceeding eleven quarter-hour periods and adds the total to obtain SUM 11. At block 210, the controller recalculates the quarter-hour running integral limit for the next quarter-hour period. (i.e., the quarter hour which starts with the next cycle through the delivery state loop.) To calculate the quarter-hour limit, the controller looks up the 3-hour and 24-hour prescription limits parameters selected by the physician and stored in the controller's RAM, and looks up SUM 11 and SUM 23 in its memory registers. SUM 11 was calculated at block 209; SUM 23 represents a count of the number of pump actuation commands which occurred in the immediately proceeding twenty-three hour periods and is calculated later in this subroutine.) The controller then calculates the number [(3-hour limit) minus (SUM 11)] and the number [(24-hour limit) minus (SUM 24)] and selects the smallest a the next quarter-hour limit. The quarter-hour limit tells the controller how many pump actuations will be allowed in the quarter hour. (NOTE: At block 161, 180, and 199, in FIGS. 11, 12 and 13 respectively, the quarter-hour limit is used to suspend pump activity when the number of pump actuations ocurring in the quarter-hour equals the quarter-hour limit).

The controller now proceeds to the segment of the housekeeping subroutine which determines whether operational anomalies have occurred during the current quarter-hour period. At block 211, a monitor report is formulated. The monitor report is an 8-bit word with each bit representing a particular type of system malfunction. At the end of the quarter-hour period, the controller surveys the pump, chamber and reservoir monitors to see if anything has gone wrong. The indicators may signify that: (1) moisture is detected in the chambers; (2) that the total number of pump actuations exceeds a certain number programmed by the physician (since the medication chamber can deliver a given number of pulses of medication, the alert tells the patient that it is time to get a medication refill); (3) that a consistency check of the data stored in the RAM indicates a change in the stored prescription parameters (Such a change may occur if, for example, a power transient or an alpha particle causes a data bit to change state. This subroutine detects any difference between the current quarter hour calculation of CHECKSUM) and the initial calculation of CHECKSUM; (4) that the current-day pump actuation monitor count is different from the number of times the controller called for pump actuation. (In the preferred embodiment the count must differ by four before an anomaly is declared); or (5) that the fluid reservoir switches indicate that reservoir is either full or overfull.

At block 212 the controller asks whether an anomaly has been previously confirmed. If an anomaly had not been confirmed we proceeds to block 213 determine whether or not an anomaly is now confirmed by the just-formulated monitor report. To confirm an anomaly the controller determines if the anomaly has occurred in two consecutive quarter-hour monitor reports and if the anomaly is one having an activated alarm criteria. (The physician can program the controller to disregard certain anomalies. If, for instance, the physician knows the moisture detector is not working properly he can have its report disregarded.)

If an anomaly is confirmed, an alarm control flag is set at 214 and the time of the first confirmed anomaly is recorded at 215. Proceeding to block 217 shown in FIG. 15, the controller asks if the alarm control flag is set. If the alarm was not set previously we skip to block 220. If the alarm flag had been previously set (i.e., set by block 214 in the current or by block 227 in the previous cycle of the delivery routine) w clear the flag at 218 and execute an alarm at 219. In the preferred embodiment, the controller actuates an alarm means which provides the patient with an electric tickle. It should be noted that other forms of alarm means, such as an audio alarm, would work equally well and are within the contemplation of the invention. The patient will receive an alarm immediately after an anomaly has been confirmed. The patient will also receive an alarm at hour intervals after the first alarm—this aspect of the program will be discussed later in this application.

At block 220 the controller asks whether the quarter-hour count is 3, 7, 11, or 15. The quarter-hour count is an integer from 0 to 15 which represents the number of quarter-hour lapsed intervals and is reset every fourth hour (i.e., at a count of 16). The actual quarter-hour counter appears later in the delivery state routine. Therefore, we answer "yes" at block 220 for the last minute of every hour of lapsed time and proceed to block 221.

The next segment of the housekeeping subroutine is encountered only during the last minute of each hour and recalculates the 24-hour running integral limit and provides other trimming and housekeeping operations. Proceeding from block 220 to block 221 the controller designates an hourly trim constant. Earlier in the delivery state routine at block 147 (see FIG. 11) we designated a pre-set nominal trim constant. Now the program selects an hourly trim constant to speed up or slow down the controller's activity so as to synchronize the controller's activity with actual time. The hourly trim constant is one of the prescription parameters which is programmable by the physician. (For example, if the oscillator clock is causing the controller to lose 30 seconds a day as compared to actual time, the physician can program a trim constant to speed up the controller during the last minute of the hour.)

The controller now proceeds to recalculate the 24-hour running integral rate limit. At block 223 the controller records in permanent RAM archives and clears from temporary registers certain information recorded during the last hour. At block 224, the controller recalculates SUM 23 which is the number of pump actuation commands issued in the immediately preceeding twenty-three. hour periods. The controller retrieves from RAM the number of pump actuation commands for each of the twenty-three preceeding hour periods and adds the total to obtain SUM 23. At 225 the controller disables the delivery interrupt feature (the delivery interrupt feature permits the physician or patient to interrupt the normal progression through the delivery state routine). The next segment of the housekeeping subroutine activates the alarm for a confirmed anomaly. As mentioned previously, the alarm means is activated on an hourly basis after an anomaly is confirmed. Therefore, at block 226 we asked whether an anomaly had been previously confirmed. If no anomaly had been previously confirmed, the controller bypasses to block 228; if an anomaly had been confirmed, the controller goes to block 227 and sets the alarm control flag. The alarm control flag will cause the alarm to be actuated at block 219 during the next cycle of the delivery state routine.

The controller now proceeds to a segment of the housekeeping subroutine which recalculates the quarter-hour limits. Since the housekeeping routine just recalculated SUM 23, it is necessary to determine if the newly determined value of that parameter changes the previous calculation of the quarter-hour limit. The controller at block 228 recalculates the quarter-hour limit using the new value for SUM 23, as calculated in block 224. The quarter-hour limit is calculated in the same manner as mentioned previously: (1) the controller looks up the 3-hour and 24-hour running integral dosage limits as programmed by the physician; (2) the controller calcules [(3-hour limit) minus (SUM 11)], and [(24-hour limit) minus (SUM 23)]; and, (3) the smaller of the two values calculated in step 2 becomes the quarter-hour limit.

The controller now proceeds to block 230, shown in FIG. 16, and provides housekeeping functions which are necessary during the last minute of every two-hour period. Proceeding now to block 230 the controller asks whether the hour count is odd, i.e., is this the last minute in an odd number hour. If we are in the last minute of an odd hour we proceed to block 231 and resynchronize the basal program element selector. (The 96-bit sequence which makes up the basal rate prescription is organized into 12 words of 8-bits each. Since each 8-bit word takes 2 hours for the controller to process, we want to select the next 8-bit word for processing during the last minute of the 2-hour lapsed period. At the beginning of the new 2-hour period we want to assure that the controller is looking at a new bit in a new basal prescription word).

The next segment of the housekeeping subroutine is only encountered during the last minute of every 4-hour time period. At block 232 we proceed to ask whether the hour counter is 3, 7, 11, 15, 19, or 23. That is to say, are we at the last minute of a 4-hour time lapse. (The hour count represents the number of lapse hours from 0 to 23 and is reset when the count reaches 24). If the answer is "yes" we proceed to block 233 and resynchronize the quarter-hour counter—the quarter-hour counter advances every 15 minutes and counts from 0 through 15 and then gets reset by block 233. The quarter-hour counter must be recycled during the last minute of a 4-hour period.

The next segment of the housekeeping subroutine is encountered only during the last minute of the day. At block 234 the controller asks if the hour count equals 23 (i.e., are we in the last minute of the day). If so, we proceed to block 235 and designate the daily trim constant. The daily trim constant is programmed by the physician and like the hourly trim constant allows the physician to speed up or slow down controller activity during a particular cycle of the delivery state routine, so as to synchronize activity with real time. Proceeding to block 236 the controller copies and clears current day archives. At 237 we ask whether we are on the last day of the month (i.e., 32-day period). If it is the last minute of the last day of the month we designate the monthly trim constant (block 238). If we are not in the last day of the month we proceed directly to block 239 and increment the day counter.

The next segment of the housekeeping subroutine can activate a noon whistle alarm. Returning to block 234 (FIG. 16), if we are not at the last minute of the day, the controller proceeds to block 240 and asks whether the hour count equals 11, i.e., is this the last minute before noon. If it is the last minute before noon we go to block 241 and ask if the physician has programmed a noon whistle. (The physician as part of the prescription parameters can request an actuation of the alarm means at noon. This can be used to assure the patient that the IPIP controller system is working). If a physician has programmed a noon whistle, the controller proceeds to block 242 and actuates the alarm means (the noon whistle in the preferred embodiment has one alarm burst whereas an anomaly alarm will be reported by several bursts from the alarm means.)

The next segment of the housekeeping subroutine initiates several counters. The controller enters block 243, shown in FIG. 16 after having completed blocks 230, 232, 240, 241, 242 or 239. At block 243 the controller increments the hourly counter (the hourly counter counts from 0 to 23) and the cumulative hourly counter (keeps track of total lapsed time in hours since the controller was put in the delivery state). Proceeding to block 244, the controller enables the delivery interrupt feature which was disabled previously at block 225 (FIG. 15).

The controller proceeds to block 245 after having exited from block 244 or block 220 (e.g., one gets to block 245 at the last minute of each quarter-hour period). At block 245, the quarter-hour count is incremented.

e. Delivery state loop housekeeping and timing segment

The controller enters the next housekeeping segment during every cycle of the delivery state loop. We can proceed to block 247 from block 245, 190, 192 or 204 (see FIG. 13 and 16), that is to say, the controller will enter block 247 during every cycle through the delivery state routine. At block 247, the minute count is incremented. Proceeding to block 248 the controller asks if the count in the minute counter exceeds 14. If so, the controller goes to block 249 and clears the minute counter. (The effect of these two steps is to reset the minute count to "0" as soon as it reaches 15). Proceeding to block 250, the controllers asks if the quarter-hour count exceeds 15; if so, the controller at block 251 clears and resets the quarter-hour counter. Similarly, proceeding to block 252 we ask if the hour count exceeds 23; if so, the hour counter is reset at block 253.

The controller must now execute a delay as required by the designated nominal, hourly, daily, or monthly trim constant. As previously discussed, the controller can specify a trim constant to override the nominal trim constant. (The nominal trim constant was set in block 147, FIG. 11). A new trim constant can be set for the cycle occuring on the last minute of the hour, day or month. At block 254 (FIG. 17), we execute the specific delay as designated earlier in the housekeeping subroutine. As mentioned previously, the trim constant delay is used as a means for synchronizing controller activity with actual time.

Proceeding to block 255, the controller asks if there are any uncompensated interrupt occurrences pending. As mentioned previously, an interrupt of the delivery cycle can be requested by the patient or physician and is used to effect some modification of drug delivery. (The Interrupt Subroutine will be discussed later in this application.) However, at present we need to know that an interrupt will delay the delivery state routine for a set number of seconds, accomplish its mission, and then permit resumption of delivery routine at the point of interruption. (The Interrupt Subroutine always takes the same amount of processing time.) If there are no uncompensated interrupts we proceed to block 258 and execute a standard delay. If there have been one more uncompensated interrupts, the delivery cycle will take several seconds longer than normal. Blocks 256 and 257 compensate by executing a shorter delay during successive cycles through the delivery routine until all such interrupts have been compensated. Block 256 decrements a counter each time the controller travels through the delivery state loop. When the number generated in block 256 equals zero, all prior interrupts have been compensated.

After completing block 258 or 257, the controller has travelled once through the delivery state loop and is ready to recycle through the loop by again performing the function in blocks 147, shown in FIG. 11. As previously mentioned, the delivery state loop, on the average, recycles once per minute, no matter what logical path is taken through the delivery state routine. The controller will continously cycle through the delivery state loop and activate the pump (when appropriate) until a transfer to the standby stat is effected.

Interrupt Subroutine

Figure 18:
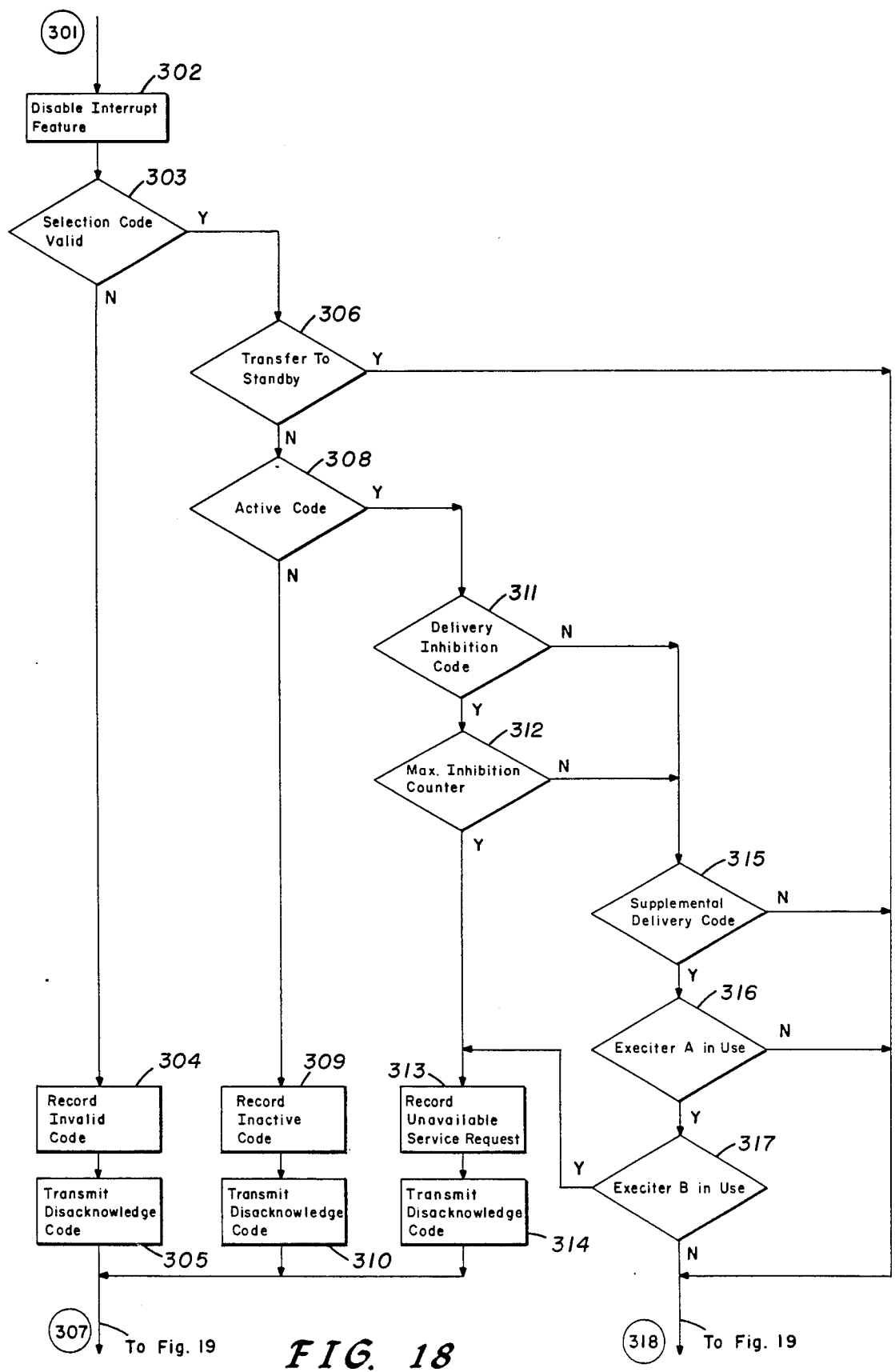
FIGS. 18 through 20 show a detailed flow chart of the interrupt subroutine.
Figure 19:
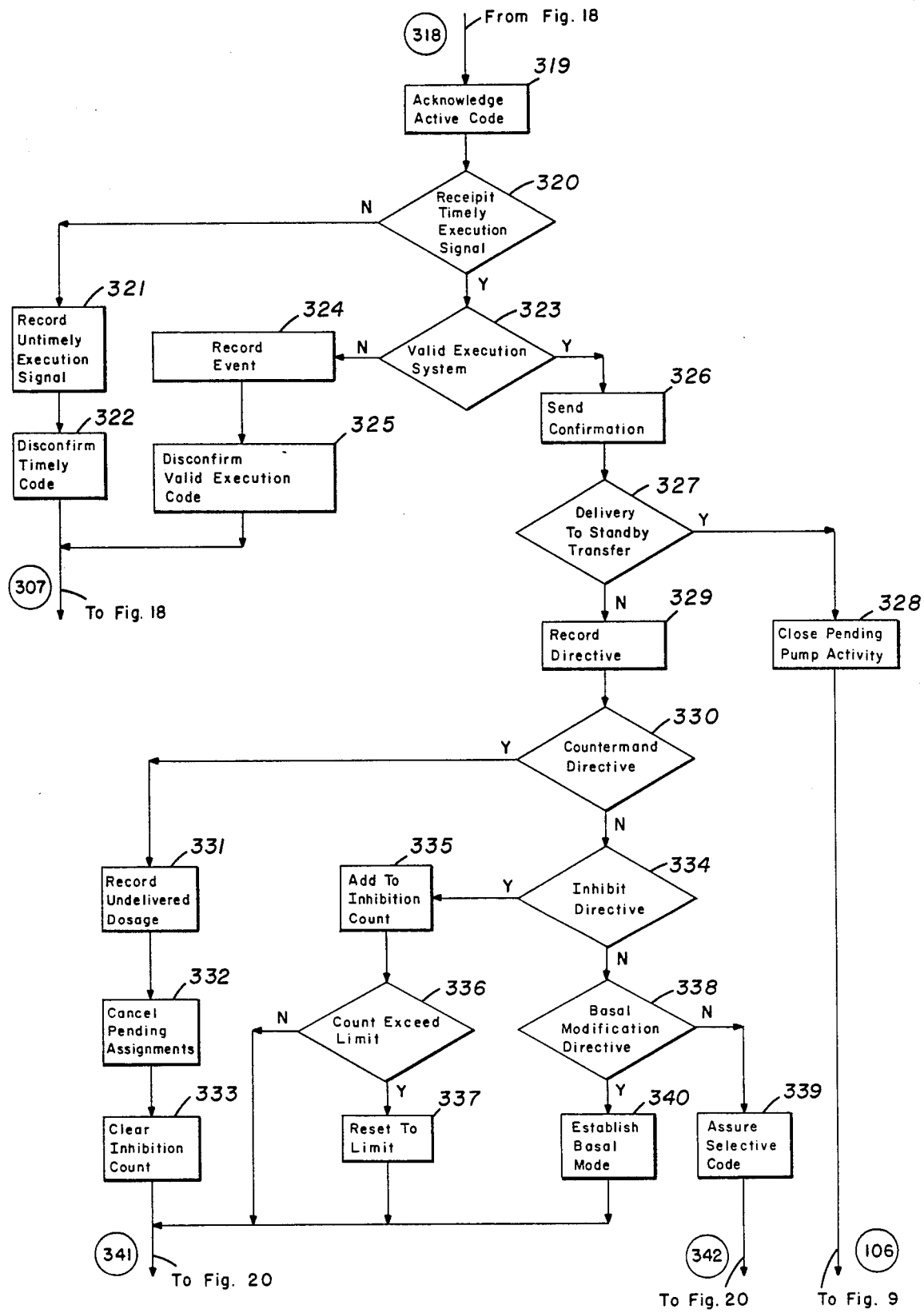
Figure 20:
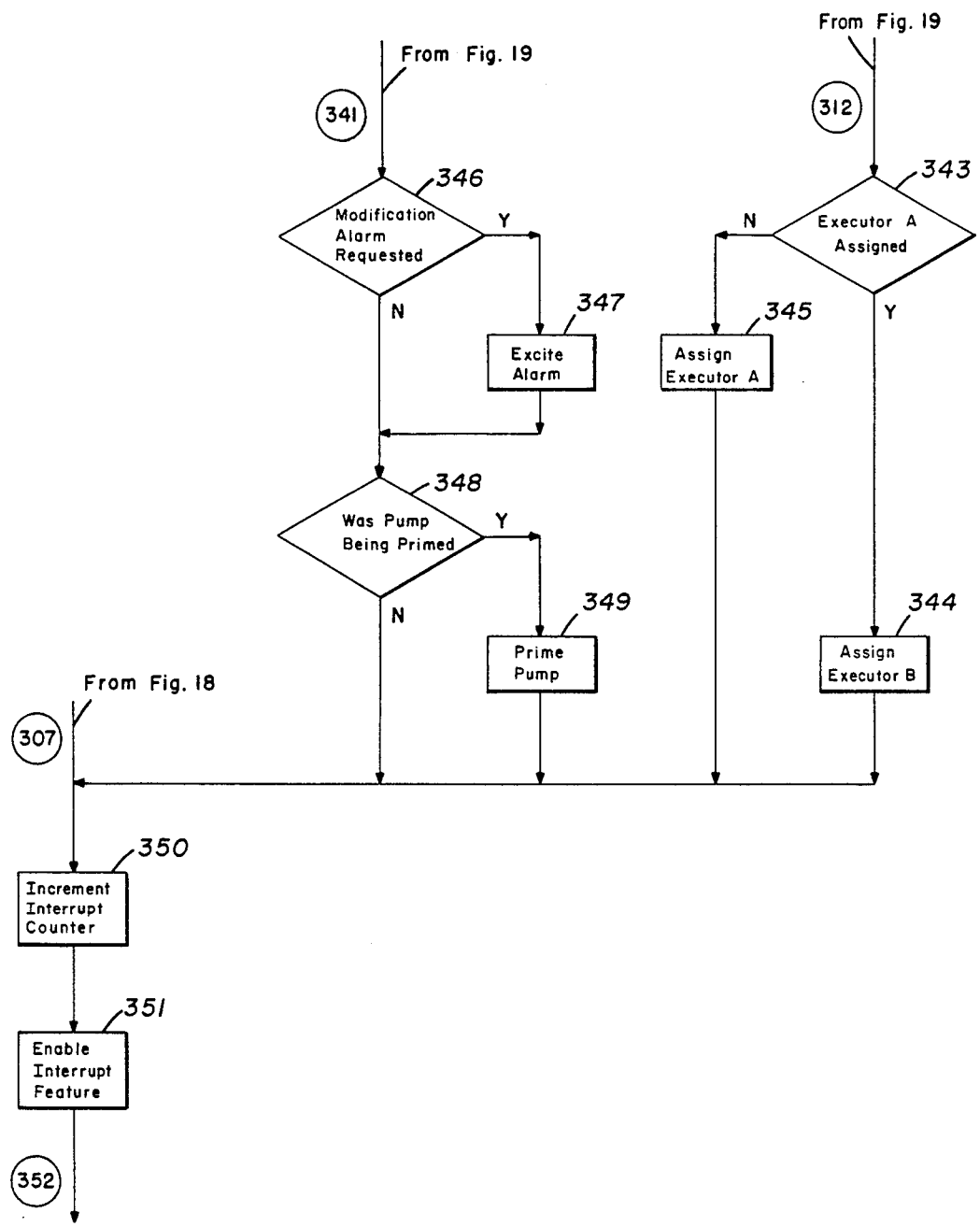

The Interrupt Subroutine flow chart is shown in FIGS. 18 through 20. This subroutine enables a physician or the patient to interrupt the delivery state loop and modify drug delivery or effect a transfer to the standby state. In operation, the PPU or MPU is used to establish a communication link with the IPIP communication means. The communication means performs certain tests to verify that an appropriate type of signal has been received (i.e., the signal must have a certain frequency and format) and conveys the received 8-bit code to the Controller's UART. When an 8-bit code is introduced into the UART the controller enters the Interrupt Subroutine at 301 to verify the receipt of a valid 8-bit delivery state selection code.

Generally, the Interrupt Subroutine can interrupt the delivery state loop at any point after the completion of any block. However, as mentioned previously, several segments in the delivery state loop have commands which prevent the controller from entering the Interrupt Subroutine during those segments. If the controller receives a transmitted code during an appropriate period in the delivery state loop, it will branch to 301, complete the Interrupt Subroutine, and return at 352 to the point at which it left the delivery state routine, and continue to recycle through the delivery state loop.

After the controller enters the Interrupt Subroutine at 301, the controller proceeds to block 302 and disables the interrupt feature (i.e., the controller is prevented thereby from accepting a second interrupt attempt while it is still processing the first interrupt).

a. Controller verifies delivery selection code

The controller proceeds to block 303 and determines whether the 8-bit code it received from the communication means represents a valid delivery state selection code. This safety feature prevents a spurious signal or an inteferring signal from accidentally modifying the prescription parameters. At block 303 the controller tests the 8-bit code to see if it represents a valid delivery state selection code. In the preferred embodiment there are a limited number of possible delivery state selection codes which instruct the controller to: (1) deliver one of the 8 supplemental prescription schedules stored in the controller's RAM; (2) deliver a half-basal schedule; (3) deliver a full basal schedule as stored in the RAM; (4) inhibit pump actuation for one hour; (5) countermand current supplemental prescription schedule assignments and any current inhibit commands; and, (6) transfer to the standby state.

The PPU is not capable of delivering the command to transfer to the standby state. The PPU can be used to select one of the supplemental prescription schedules previously stored by the physician in the controller's RAM. Similarly, the PPU can select either full or half-rate delivery of the basal prescription schedule previously stored by the physician in the controller's RAM. The PPU can also be used to inhibit pump actuation for up to 8 one-hour periods, or to countermand certain previous commands made by the PPU.

Returning to the flow chart in FIG. 18, if the controller at block 303 finds an invalid selection code it proceeds to record in RAM the receipt of an invalid code (block 304) and disacknowledges receipt of a valid selection code (block 305). In the preferred embodiment, to disacknowledge receipt of a valid selection code, the controller transmits to the PPU or MPU a disacknowledgement code. Returning to block 303, if the controller receives a valid code we proceed to block 306 and ask if a delivery to standby state transfer was requested. If such a transfer was requested we branch to block 319 (FIG. 19); if not, we proceed to block 308.

b. Controller tests deliverability of selection code

At block 308, the controller asks if the selection code is an active selection code (i.e., not inhibited by the physician's prescription). The physician, as part of the prescription parameters, can deactivate any of the PPU selection codes. (For example, the physician may not want the patient to use the inhibit selection code. If the physician deactivates this selection code, the controller at block 308 would not identify the inhibit selection code as an active code.) If at block 308 the controller finds an inactive code, it branches to blocks 309 and 310, recording receipt of the inactive selection code and transmitting a disacknowledging signal.

If, however, the selection code is active the controller proceeds to block 311 and the controller determines if the selection code requests delivery inhibition. If delivery inhibition is selected, the controller proceeds to block 312 and asks if the inhibition period is at the maximum possible level. In the preferred embodiment, the maximum inhibition period is 8 hours (i.e., 32 quarter-hour periods). Each time the patient uses the inhibit selection code one hour's (4 quarter-hour periods) worth of inhibition is provided. A counter, which we discussed in the delivery state loop, keeps track of the number of quarter-hour periods calling for inhibition. If the counter exceeds 32, the controller proceeds to block 313 and 314 recording the request for unavailable inhibition service and sending a disacknowledgement to the PPU. However, if selection code did not call for inhibition (block 311) or, the maximum inhibition period was not exceeded (block 312), the controller proceeds to block 315. At block 315 the controller determines whether the selection code calls for execution of a supplemental prescription schedule, and if so the controller proceeds to blocks 316 and 317 to determine if Executor A or Executor B are currently under assignment. If both Executor A and B are in use, the controller proceeds to block 313 and 314, recording that the requested supplemental prescription schedule cannot be currently executed and sending a disacknowledgement to the PPU. If however, either Executor A or B are available, the supplemental prescription scheduled can be delivered and the controller proceeds to 319 (FIG. 19).

c. Double handshaking means

It will be noted at this point in the Interrupt Subroutine, that the controller has tested the selection code and is satisfied that the selection code is valid, active, and requests a service that the controller can currently provide. The controller now proceeds at block 319 (see FIG. 19) to acknowledge to the PPU or MPU receipt of a valid and active selection code representing a request which can be fulfilled. The controller provides this acknowledgement by transmitting a preamble and repeating the received selection code for verification by the PPU or MPU. The PPU or MPU then verifies that the acknowledgment corresponds to the intended selection code. If there is a verification, the MPU or PPU sends an 8-bit execution signal. At block 320 the controller asks if this execution signal has been received before the expiration of a time limit. This safety feature assures that the correct selection code has been received by the IPIP, and it also prevents spurious or interfering signals from modifying prescription commands.

If the execution signal was not timely received, the controller at block 321 records the failure to receive a timely execution signal and at the block 322 transmits a signal disconfirming receipt of a timely execution code. However, if a timely execution code is received the controller asks at block 323 if the execution code has the prescribed structure—again, protecting the IPIP from being influenced by spurious signal. If a valid execution code is not received, the controller records receipt of an erroneous signal at block 324 and transmits a disconfirmation code (block 325). If however, a valid and timely execution code is received the controller proceeds to block 326 and instructs the communication means to send a signal to the PPU or MPU confirming receipt of a valid and timely execution code.

d. Controller performs and records the selection code and alerts patient to unusual modifications At this point in the Interrupt Subroutine, the controller is now satisfied that the original selection code is not only active and valid, but that the request implied by receipt of that selection code should be honored. Proceeding to block 327, the controller asks if the selection code requests transfer to the standby state. (It will noted that only the MPU has the capability of transmitting the selection code which can transfer the controller from the delivery to the standby state. Limiting the PPU's prescription programming capability is a safety feature preventing the patient from inadvertently or intentionally exceeding safe dosage limits.) If the controller is requested to transfer from the delivery to the standby state, it terminates any pending pump activity (block 328). The controller might have been priming the pump when interrupt was initiated. The controller then proceeds at 106 (see FIG. 9) to enter the standby state.

If, however, the selection code does not request such a transfer, the remaining selection codes must request a delivery state controller directive; therefore, at block 329 the controller records receipt of a selection code modifying a medication dosage. (This information is recorded in the RAM and can be retrieved by the physician to assess if the patient is using the device appropriately). Proceeding to block 330, the controller asks if the selection code constitutes a request to countermand a pending medication selection directive; and, if so, the controller proceeds to blocks 331, 332 and 333. The controller records the supplemental prescription schedule dosages which will be undelivered (block 331), cancels the current supplemental prescription schedule assignments to Executor A or B (block 332), and clears the pending inhbihition count (block 333). If the patient had previously called for one or more hours of pump inhibition, clearing the inhibition counter will have the effect of countermanding the previous inhibition commands.

If, however, the selection code was not a countermand directive, the controller proceeds to block 334 and asks if the selection code corresponds to an inhibition directive. (In the preferred embodiment the inhibition directive allows the patient to suspend medication delivery for one hour. The patient can only deliver 8 such consecutive inhibition commands.) If the selection code requests inhibition, the controller proceeds to block 335 and adds four quarter-hour counts to any pending inhibition period count. Proceeding to block 336, the controller asks if the inhibition count exceeds a maximum permissible level. (i.e., does the count exceed 32 quarter-hour periods.) If the counter exceeds the maximum limit the count is reduced to the maximum limit at block 337.

Returning to block 334, if the selection code is not an inhibit directive, the controller proceeds to block 338 and asks if the code represents a modification of the basal delivery schedule (i.e., a command to deliver half basal, or a command to deliver full basal). If the selection code does not call for a basal modification, the controller proceeds to block 339 and assures that the selection code constitutes a request to deliver a supplemental prescription schedule and exits at 342 to a point in the subroutine shown in FIG. 20. (If the selection code becomes inadvertently modified, block 339 sets the code to one of the supplemental prescription schedule selections by ignoring unused bits in the selection code.) If, however, the controller determines at block 338 that a basal directive was requested, the controller proceeds to block 340 and establishes the requested half or full basal delivery.

The Interrupt Subroutine flow chart continues in FIG. 20. The controller proceeds to block 343 if the selection code calls for an assignment of a supplemental prescription schedule. At block 343, the controller asks if Executor A has been assigned and if so the controller assigns (block 344) the new supplemental prescription schedule to Executor B; if however, Executor A was not assigned, the controller assigns (block 345) the supplemental prescription schedule to Executor A.

Alternatively, the controller could have entered block 346 after having passed through blocks 333, 336, 337, or 340 (see FIG. 19). If the controller took this route, it means the selection code requested a basal delivery modification (i.e., half or full basal delivery), or an inhibit or countermand directive. Since the basal selection directive, inhibit directive, and countermand directive are not normally used by the patient, it may be advisable to alert the patient that such a selection had been made. This is an additional safety feature which assures that an inadvertent patient error will not alter the patient's medication schedule. At block 346, the controller asks if the prescription calls for an alarm if particular prescription modifications are requested. If such an alarm is prescribed, the controller (block 347) executes a single burst alarm. Proceeding to block 348, the controller asks if the pump was being primed prior to the Interrupt Subroutine. If the answer to block 348 is "yes", the pump is again primed (block 349). This feature is necessary because in the preferred embodiment the voltage quadrupler is used both to energize the alarm and to prime the pump. Since in blocks 346 and 347 the quadrupler could have been used to energize the alarm, it may now be necessary to re-energize the pump priming means.

The controller will now enter block 350 irregardless of the pass taken through the Interrupt Subroutine, unless the selection code requested a transfer from the delivery to the standby state. (The controller can arrive at block 350 after processing blocks 348, 349, 345, 344, 305, 310, 314, 322, or 325, see FIGS. 18-20). The controller at block 350 must now increment the uncompensated interrupt occurrence counter. The uncompensated interrupt occurrence counter was discussed previously in the delivery state loop and is used by the controller at block 257 (FIG. 17), to compensate for delay in the one-minute delivery state loop caused by an Interrupt Subroutine. (In the preferred embodiment, the time compensation is accomplished over several cycles of the delivery state loop.) The controller now proceeds to block 351 and enables the delivery interrupt feature which was previously disenabled at block 302 (FIG. 18). The Interrupt Subroutine is now complete and at 352 the controller returns to the delivery state loop at the same point it had previously exited to perform the Interrupt Subroutine. The controller, now in the delivery state mode, continues to cycle through the delivery state loop providing medication dosages as requested by the selected supplemental or basal prescription schedules.

Performance of Running Integral Dosage Limit Means

The running integral dosage limit means enables the controller to suspend pump actuation when the dosage in a prescribed time period exceeds a limit. In the preferred embodiment a 3-hour and a 24-hour time window is used. The physician as part of the prescription parameter, programs the maximum dosage of medication (i.e., number of pump actuations) allowable in the 3-hour and 24-hour period. The 3-hour time window is shifted by the controller every quarter hour; the 24-hour time window is shifted every hour.

The running integral limit calculation means (outlined in FIG. 8, with the detailed software flow chart shown in FIGS. 14 and 15) calculates the number of pump actuations allowable in the next quarter-hour period. The controller keeps a record of the number of pump actuations which have occurred in each quarter hour period. A segment of the software routine retrieves this data from RAM archives and calculates the number of pump actuations occurring in the most recent eleven quarter-hour periods (SUM 11) and the most recent twenty-three hour periods (SUM 23). As discussed previously, SUM 11 and SUM 23 are subtracted from the 3-hour programmed limit and the 24-hour programmed limit. The smaller of [(3-hour limit) minus (SUM 11)] or [(24-hour limit) minus (SUM 23)], for a particular quarter-hour, is set as the quarter-hour running integral limit. In effect, the controller shifts a time window at quarter-hour intervals and determines if any additional pump actuations will be allowable in the next quarter-hour period.

The quarter-hour running integral limit means is included in Executor A, Executor B and the basal delivery subroutine (the quarter-hour running integral limit means is outlined in FIG. 8 and its detailed software flow chart is shown in FIGS. 11 through 13). If the total pump actuations in the current quarter-hour equals the quarter-hour running integral limit, the controller branches around the pump priming function and pump actuation is avoided.

Figure 21:
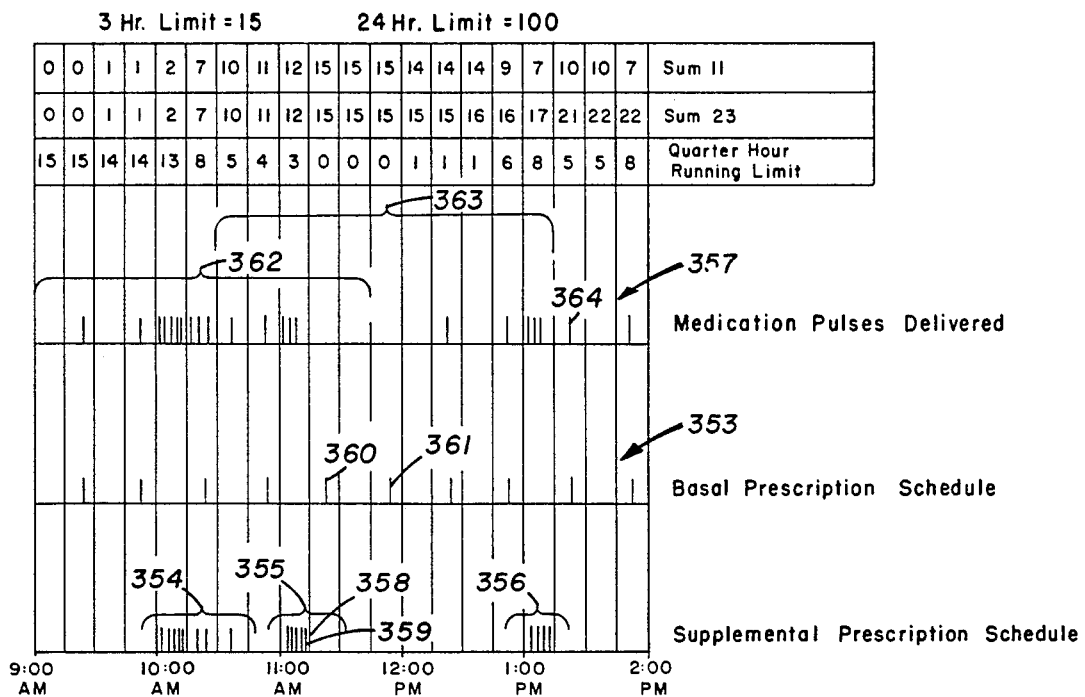
FIG. 21 is a functional illustration of the running integral dosage limiting means inhibiting an inappropriate dosage delivery.

FIG. 21 illustrates a typical application of the running integral dosage limit means to monitor an infusion pump used to deliver insulin to a diabetic patient. The physician has programmed a basal prescription dosage 353, which calls for pump actuation every 30 minutes. Supplemental prescription schedules have also been programmed by the physician and can be requested by the patient using the PPU. The patient will request a supplemental prescription schedule before each meal so that the postprandial insulin delivery profile will be increased. The physician aware of the particular patient's physiology has programmed a 3-hour running integral dosage limit of 15 pump actuations and a 24-hour running integral dosage limit of 100 pump actuations.

In the example shown in FIG. 21, the patient requests three supplemental prescription schedule assignments. The first assignment 354 is requested before the breakfast meal at approximately 10 a.m. A second supplemental prescription schedule 355 is requested at 11 a.m. after the patient has eaten a snack, and a third supplemental prescription schedule 356 is requested at 1 p.m. before the patient eats lunch.

The actual medication dosage delivered by the infusion pump is shown in FIG. 21 on line graph 357. However, it will be noted that the running integral limit means has prevented four pulses of medication (358–361) from being delivered. The requested breakfast supplemental prescription schedule 354 and snack supplemental prescription schedule 355 would have resulted in excess dosage over a 3-hour period if the running integral limit means had not been in effect. (In the example shown in FIG. 21, it is assumed that for simplicity, the pump was implanted at 9 a.m. and no pump actuations occurred prior to 9 a.m.)

FIG. 21 clearly shows the useful effect obtained by using a running integral dosage limit means. A 3-hour window shown at 362, contains a count of 15-pump actuations. Since the 3-hour limit is 15, the quarter-hour running integral rate limit for the next quarter-hour is zero, and as a result the pump actuation 361 requested by the basal prescription schedule is not deliverable. Looking at another 3-hour time period (shown at 363) the number of pump actuations occurring during that period was eleven, therefore, the next quarter-hour period would allow delivery of 4 pulses of medication. Therefore, a pulse of medication 364 requested by the basal prescription schedule during that next quarter-hour period is now allowable.

The running integral dosage limit means which was described and claimed in the U.S. parent application, contains both a hardware and software system. The current embodiment is a total programmable software version. It is within the contemplation of the inventor to use the integrated rate limit means in either an implanted or an external infusion pump. The invention represents a unique safety feature which allows flexibility in dosage programming and at the same time prevents an inadvertent or intentional overdose.

Digital Integrating Rate Limiter

In the preferred embodiment, a hardwired digital integrating rate limiter is used in combination with the software running integral dosage limit means. The digital integrating rate limiter is a separate backup system independent of the microprocessor operation. The digital integrating rate limiter is used to set an outer envelope of allowable dosages. In the preferred embodiment, this maximum envelope of allowable dosages will only be reached if a software system failure allows the pump to be acutated at a dangerously high rate.

Figure 22:
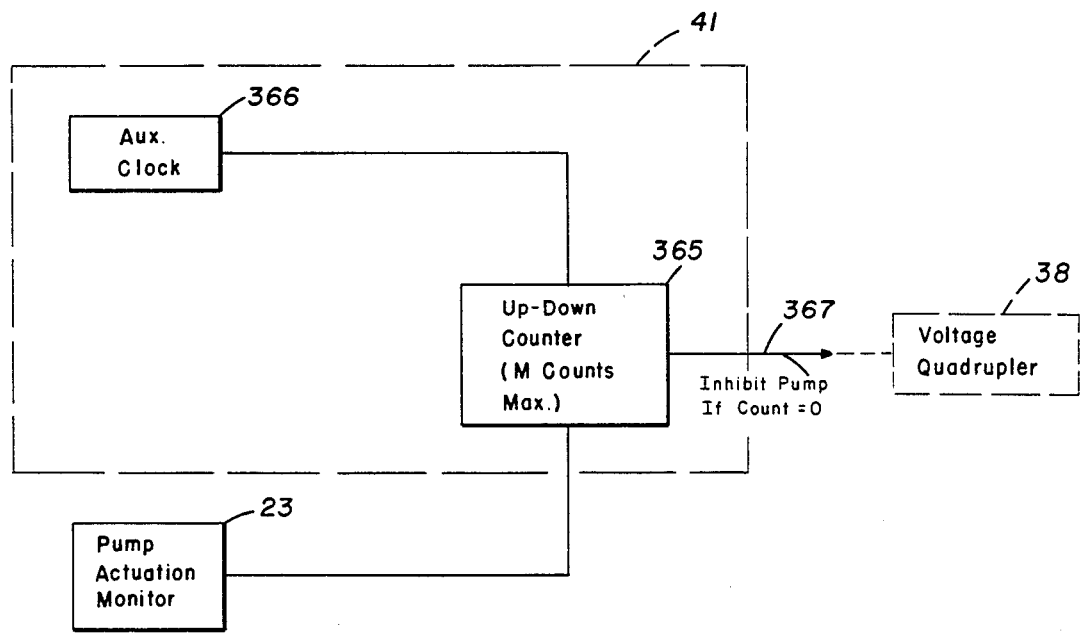
FIG. 22 is a block diagrammatic view of the digital integrating rate limiter.

A block diagram of the digital integrating rate limiter 41 is shown in FIG. 22. Generally, the digital integrating rate limiter comprises: (1) an updown counter 365 capable of storing M counts; (2) a clock 366 capable of delivering N counts/hour (in the preferred embodiment, a separate auxiliary RC oscillator, separate from the microprocessor's clock, provides the clock pulses to the digital integrating rate limiter); and, (3) a pump actuation monitor 23, which provides a pulse each time the pump means 18 (see FIG. 2) actually delivers medication. The updown counter provides signal 367 which inhibits pump actuation, when its counter is zero. Pump priming will be inhibited if M+N pulses are delivered the first hour, and if N pulses are delivered per hour thereafter.

The operation of the digital integrating rate limiter might best be viewed in terms of the following simple example. A updown counter is initially full with M counts. The clock causes additional counts to flow into the updown counter at the rate of N counts per minute. If the updown counter is at its maximum full capacity, the additional counts will be disregarded; however, if the updown counter is not full, the counts will be added until the updown counter has reached its maximum of M counts. The pump actuation monitor subtracts pulses each time the pump is actually triggered. The pump counts subtract from the counts contained in the updown counter. In operation, the updown counter can be emptied of counts as rapidly as possible until no counts remain. If no counts remain (i.e., the updown counter is at zero), the pump actuation will be inhibited. If less than the full number of counts are drawn from the updown counter—if, for example, a supplemental prescription schedule calls for 15 counts to be delivered in the first hour, and a basal rate of a 5-counts per hour thereafter—the clock will slowly fill the updown counter back to its maximum capacity of M counts.

Therefore, the pump can be called to deliver a large dosage of medication at one particular time. The pump will be allowed to deliver medication until it depletes the updown counter of counts. (i.e., until the updown counter reads zero.) In addition to a maximum dosage delivery in a short period of time the pump can deliver a basal rate dosage of medication. As long as the basal rate is less than the clock rate (N pulses per hour), the updown counter will be slowly refilled so that an additional large dosage can be delivered in the future—i.e., when the patient requests delivery of an additional supplemental prescription schedule.

In the preferred embodiment, the updown counter 365 is a 5-bit counter which can hold a maximum of 32 pulses. When the counter is zero, a signal 367 is sent to the voltage quadrupler 38 thereby inhibiting pump priming. In this embodiment, the pump can delivery a maximum of 42 pulses of medication in the first hour and continue to deliver a constant basal rate at 11 pulses per hour thereafter. This outer limit was selected for infusion pumps used by diabetics because it represents the maximum concentration of insulin a patient can safely tolerate. It assumes that a physician will prescribe a basal rate of less than 11 pumps per hour and a supplemental prescription schedule which requires the delivery of less than 43 pumps of medication. It is to be understood that the outer dosage limit depends on the type of medication, the concentration of medication, and the volume of medication delivered by each pump actuation. Therefore, it is within the contemplation of this invention to provide different maximum dosage envelopes by adjusting the clock rate (N pulses per hour) and adjusting the maximum count in the updown counter (M counts).

Although the preferred embodiment utilizes the digital integrating rate limiter as a backup system which is used in combination with the software running integral dose limits means, the invention contemplates an infusion pump in which the digital integrating rate limiter is the sole means of providing protection against inadvertent or intentional medication overdoses. It is also envisioned that the maximum storage capacity of the updown counter can be programmable by the physician to provide flexibility for different patients. It is also within the contemplation of the invention to provide a programmable clock which can be modified to allow a smaller or larger basal delivery of medication.

While there have been described what are believed to be the preferred software and hardware embodiments of the invention, those skilled in the art will recognize that other and further modifications may be made hereto without departing from the spirit of the invention, and it is intended to claim all such embodiments as fall within the true scope of the invention.

Having set forth the nature of the invention, what is claimed is:

1. A medication infusion apparatus having a controller to actuate a pump means, said controller comprising:
   a memory means for storing a basal prescription program, said basal prescription program automatically requesting basal delivery of medication to change to preset rates at pre-programmed intervals during a significant periodic physiologic cycle;
   a basal delivery means operably coupled to said memory means and said pump means for actuating said pump means in accordance with said basal prescription program, thereby generating a programmed basal dosage profile;
   a second memory means for storing supplemental prescription schedules, each of said supplemental prescription schedules comprising a program to sequence pump means actuation over preselected time intervals;
   a patient supplemental command means for selecting one of said supplemental prescription schedules from said second memory means, said patient supplemental command means being manually initiated by the patient;
   a supplemental delivery means for actuating said pump means in accordance with said selected supplemental prescription schedule, wherein said pump means causes a fixed volumetric dosage of medication to be delivered with each pump means actuation; and,
   a running integral dosage limiting means operably coupled to said basal delivery means and supplemental delivery means for creating and updating a current shifting time window of preselected length, for summing the number of pump means actuation occurring within said current time window of preselected length and for inhibiting pump means actuation while said sum exceeds a running integral dose limit.

2. The apparatus as in claim 1 further comprising a physician command means for programming said running integral dose limiting means with at least one running integral dosage limit, said physician command means being manually.

3. The apparatus of claim 1, wherein said time window of preselected length is a three (3) hour window and wherein runing integral dosage limiting means sums the number of pump means actuations occurring in the most recent 3-hour time period, and inhbiits pump means actuation if said sum exceeds a 3-hour running integral dosage limit.

4. The apparatus of claim 3, wherein said running integral dosage limiting means further comprises a second inhibiting means for summing the number of pump means actuations occurring in the most recent 24-hour time period and inhibiting pump means actuation if said sum exceeds a 24-hour running integral dosage limit.

5. The apparatus of claim 1, wherein each actuation of said pump means delivers a fixed volumetric dosage of medication and wherein said running integral dosage limiting means comprises a means responsive to actual pump means operation for summing the number of actual operations of said pump means within said current time window.

6. The apparatus of claim 1 wherein each actuation of said pump means delivers a fixed volumetric dosage of medication and wherein said basal delivery means and said supplemental prescription delivery means comprises a means for generating an actuation request for each intended pump means actuation, and wherein said running integral dosage limiting means comprises a means for summing the number of actuation requests generated within said current time window.

7. A medication infusion apparatus having a controller to actuate a pump means, said controller comprising:
   a memory means for storing a basal prescription program, said basal prescription program automatically requesting basal delivery of medication to change to preset rates at pre-programmed intervals during a significant periodic physiologic cycle;
   a basal delivery means operably coupled to said memory means and said pump means for actuating said pump means in accordance with said basal prescription program, thereby generating a programmed basal dosage profile; and,
   a hardwired incremental integrating rate limit means for inhibiting pump means actuation when a certain maximum dosage envelope is exceeded.

8. A medication infusion system having a controller to actuate a pump for injection of medication into a selected site in a patient, said controller comprising:
   a delivery means for actuating said pump in accordance with a selectable dosage schedule; and,
   a limiting means for monitoring medication delivery and for inhibiting actuation of said pump by said delivery means when said medication delivery exceeds a dosage limit.

9. The apparatus of claim 8, wherein said limiting means comprises:
   a running integral dosage limiting means for creating and updating a current shifting time window of preselected length, for determining the amount of medication delivery by said medication infusion system said current time window of preselected length and for inhibiting actuation of said pump while said determined amount exceeds a running integral dosage limit.

10. The apparatus of claim 9, wherein each actuation of said pump delivers a fixed volumetric dosage of medication, and wherein said running integral dosage limiting means comprises a means for summing the number of pump actuations within said current time window to determine the amount of medication delivery in said current time window.

11. The apparatus of claim 9 or 10, wherein said running integral dosage limiting means includes a programmable means for variably adjusting said running integral dosage limit.

12. The apparatus of claim 9 wherein with each actuation of said pump said pump operates to deliver a fixed volumetric dosage of medication and wherein said running integral dosage limiting means comprises a means responsive to pump operation for summing the number of actuations of said pump within said current time window to determine said amount of medication delivery in said current time window.

13. The apparatus of claim 8, wherein said limiting means comprises:
an incremental integrating rate limiting means for inhibiting pump actuation when a certain maximum dosage envelope is exceeded.

14. The apparatus of claim 8, wherein said limiting means further comprises an incremental integrating rate limiting means, said incrmental integrating rate limiting means comprising:
a pump monitor means for providing a pulse each time said pump delivers a fixed volumetric dosage of medication;
a clock capable of delivering N pulses per hour; and, counter means for storing M counts, operably connected to said clock and said pump monitor means, said counter means initially set at M counts, wherein said counter means includes a means for reducing said counter means by one count for each pulse from said pump monitor means, and a means for increasing said counter means by one count up to the maximum M count for each pulse from said clock, and wherein said counter means further includes a means for inhibiting pump actuation when said count is zero.

15. The apparatus of claim 14, wherein each actuation of said pump delivers a fixed volumetric dosage of medication, and wherein said pump monitor means provides a pulse for each pump actuation attempted by said delivery means.

16. The apparatus of claim 14, wherein said updown counter includes a means for variably adjusting the maximum storage capacity M of said updown counter.

17. The apparatus of claim 14, wherein said clock includes a means for variably adjusting the pulse per hour rate N of said clock.

18. The apparatus of claim 8, wherein said delivery means further comprises:
a memory;
a first control means operably associated with said memory and manually operable for storing a plurality of dosage schedules in said memory;
a second control means operably associated with said memory and said first control means and manually operable for selecting one of said dosage schedules stored in said memory, wherein said delivery means activates said pump in accordance with said selected dosage schedule.

19. The apparatus of claim 8, wherein said delivery means further comprises a means manually operable for selecting a predetermined dosage schedule, said predetermined dosage schedule causing said pump to be actuated in accordance with a certain sequence; and, a control means manually operably for modifying said sequence of pump actuations within certain predetermined limits.

20. The apparatus of claim 8, wherein each actuation of said pump delivers a fixed volumetric dosage of medication, wherein said delivery means comprises a means for generating an actuation command for each intended pump actuation in accordance with said selectable dosage schedule, and wherein said limiting means comprises a running integral dosage limiting means for creating and updating a current shifting time window of preselected length, for summing the number of actuation commands generated within said current time window to determine said medication delivery and for inhibiting actuation of said pump while said sum exceeds a running integral dosage limit.

21. The apparatus of claim 20, said implanted portion further comprising:
at least one monitor means for detecting an anomaly in the medication infusion system;
an alarm means; and,
an anomaly alert means for periodically reviewing said at least one monitor and for actuating said alarm means if an anomaly is detected.

22. The apparatus of claim 21, wherein said anomaly monitor means comprises a means for detecting the presence of moisture in a particular portion of said medication infusion system.

23. The apparatus of claim 21, wherein said anomaly monitor means comprises a means for detecting when said reservoir is empty.

24. The apparatus of claim 21, wherein said anomaly monitor means comprises a means for detecting when said reservoir is too full.

25. The apparatus of claim 21, wherein said anomaly monitor means comprises a means for counting the number of actual pump actuations, for counting the number of times the basal and supplemental delivery means request an actuation of said pump means, and for generating an alert signal when there is a discrepancy between said actual pump actuation means count and said basal and supplemental delivery means requested actuation count.

26. The apparatus of claim 21, wherein said anomaly alerting means further comprises a means for checking supplemental prescriptions schedules stored in said memory means, and determining if said supplemental prescription schedules have been altered.

27. The apparatus of claim 21, wherein said anomaly alert means comprises a means for confirming an anomaly by requiring two consecutive anomaly reports from said at least one monitor means before actuating said alarm means.

28. The apparatus of claim 21, wherein said alarm means generates an audio signal.

29. The apparatus of claim 21, wherein said alarm means generates a subcutaneous electrical stimulation.

30. A medication infusion system having a controller to actuate an infusion pump means for infusion of medication into a selected site in a patient, said controller comprising:
a microprocessor;
a pump means operably controlled by said microprocessor for selectively delivering medication to said patient;

a memory means operably associated with said microprocessor for storing prescription parameters; and wherein said microprocessor comprises:

a control means operably connected to said memory means for selecting at least one of said prescription parameters from said memory means;

a delivery state subroutine means for providing actuation commands to said pump means in accordance with said at least one selected prescription parameter, and;

a limiting means operably coupled to said delivery state subroutine means for inhibiting said pump means actuation commands when medication delivery requested by said delivery state subroutine means exceeds a dosage limit.

31. The apparatus of claim 30 wherein said microprocessor further comprises:

an interrupt subroutine means for storing said prescription parameters into said memory means, said prescription parameters including at least one prescription schedule and a selection code, wherein said selection code causes said interrupt subroutine means to assign a particular one of said at least one prescription schedule to be processed by said delivery state subroutine means.

32. The apparatus of claim 30 or 31, wherein said limiting means comprises:

a means for creating and updating a current shifting time window of preselected length;

a summing means response to said means for creating and updating for counting the number of pump means actuation commands made by said delivery state subroutine means during the most recent shifting time window of preselected length, each actuation of said pump means delivering a fixed volumetric dosage of medication; and, a means for inhibiting actuation of said pump means by said delivery state subroutine means while said sum exceeds a runnning integral dosage limit.

33. A method of infusing medication into a patient, wherein a controller actuates a pump in accordance with a prescription schedule, said method comprising the steps of:

recording prescription schedules in a memory associated with said controller;

selecting from said memory a particular one of said prescription schedules to be delivered by said controller;

delivering medication in accordance with said selected prescription schedule, wherein said controller applies an actuating voltage to said pump at the appropriate times indicated in said selected prescription schedule, said pump causing a fixed volumetric dosage of medication to be delivered with each actuation of said pump;

creating and updating a shifting time window of preselected length to generate a current time window;

summing the number of times said actuating voltage is applied to said pump by said controller during said current time window; and, inhibiting actuation of said pump while said sum exceeds a dosage limit.

34. The method of claim 33, wherein said dosage limit is fixed.

35. The method of claim 33, further comprising the step of setting the value of said dosage limit.

36. The method of claim 33, further comprising the step of programming the value of said dosage limit.

37. The method of claim 33 further comprising the step of:

programming said dosage limit, wherein said programming step is restricted so that only attending medical staff can program said dosage limit.

38. The method of claim 33, wherein said inhibiting step further comprises inhibiting pump actuation when a maximum dosage envelope is exceeded.

39. The method of claim 38, wherein said step of inhibiting pump actuation when a maximum dosage envelope is exceeded, further comprises the steps of:

setting an updown counter with a maximum M count;

subtracting one count from said updown counter each time said pump is operated;

adding one count to said updown counter at a clocking rate of N counts per hour until said updown counter reaches said maximum count of M; and, inhibiting pump actuation while said updown counter has a count of zero.

40. The method of claim 39, wherein said maximum count M and said clocking rate of N counts per hour, are set prior to assembly of said medication infusion system.

41. The method of claim 39, further comprising the step of setting said clocking rate to deliver N counts per hour.

42. The method of claim 41, wherein said maximum count M and said clocking rate of N counts per hour are set by the attending medical staff.

43. The method of claim 39, further comprising the step of programming said maximum count M and said clocking rate of N counts per hour, wherein said step is restricted so that only attending medical staff can program said maximum count M an said clocking rate of N counts per hour.

44. A method for limiting the amount of medication delivered to a patient by a medication infusion system, wherein said medication infusion system comprises a controller to actuate a pump in accordance with parameters, said method comprising the steps of:

creating and updating a shifting time window of preselected length to generate a current time window;

determining the amount of medication delivery by said medication infusion system during said current time window to generate a current dosage sum; and, inhibiting actuation of said pump while said sum exceeds a dosage limit.

45. The method of claim 44, wherein each actuation of said pump delivers a fixed volumetric dosage of medication, and said step of determining the amount of medication delivery is enacted by summing the number of pump actuations during said current time window.

46. The method of claim 45, wherein said step of summing pump actuations involves summing the number of times said pump operates.

47. The method of claim 45, wherein said step of summing pump actuations involves summing intended actuations of said pump by said controller.

48. The method of claim 44, wherein said dosage limit is set prior to assembly of said medication infusion system.

49. The method of claim 44, further comprising the step of selecting the value of said dosage limit.

50. The method of claim 44 further comprises the step of programming said dosage limit, wherein said step is restricted so that only attending medical staff can program said dosage limit.

51. A method for limiting the amount of medication delivered to a patient by a medication infusion system, wherein said medication infusion system comprises a controller to actuate a pump in accordance with prescription parameters, said method comprising the steps of:

setting an updown counter with a maximum M count;

subtracting one count from said updown counter each time said pump causes a fixed volumetric dosage of medication to be delivered;

adding counts to said updown counter at a clocking rate of N counts per hour until said updown counter reaches said maximum count of M; and, inhibiting pump actuation while said updown counter has a count of zero.

52. The method of claim 51, wherein each actuation of said pump delivers a fixed volumetric dosage of medication, and wherein said step of subtracting involves subtracting one count from said updown counter for each pump actuation.

53. The method of claim 52, wherein said step of subtracting involves subtracting one count each time said pump operates.

54. The method of claim 52, wherein said step of subtracting involves subtracting one count for each intended actuation of said pump by said controller.

55. The method of claim 51 or 52, wherein said maximum count M and said clocking rate of N counts per hour are set prior to assembly of said medication infusion system.

56. The method of claim 51 or 52, wherein said maximum count M and said clocking rate of N counts per hour are set by attending medical staff.

57. The method of claim 51 or 52, further comprising the step of setting the value of said clocking rate.

58. The method of claim 51, further comprising the step of programming said maximum count M and said clocking rate of N counts per hour, wherein said programming step is restricted so that only attending medical staff can program said maximum count M and said clocking rate of N counts per hour.

59. The method of claim 44 or 51, wherein said medication infusion system is adaptable to be implanted in said patient.

60. The method of claim 44 or 51, wherein said medication infusion system is adaptable to be located external to said patient.

61. A medication infusion apparatus having a controller to actuated a pump means, said controller comprising:

a memory means for storing a basal prescription program, said basal prescription program automatically requesting basal delivery of medication to change to preset rates at pre-programmed intervals during a significant periodic physiologic cycle;

a basal delivery means operable coupled to said memory means and said pump means for actuating said pump means in accordance with said basal prescription program, thereby generating a programmed basal dosage profile;

a second memory means for storing supplemental prescription schedules, each of said supplemental prescription schedules comprising a program to sequence pump means actuation over preselected time intervals;

a patient supplemental command means for selecting one of said supplemental prescription schedules from said second memory means, said patient supplemental command means being manually initiated by the patient; and a supplemental delivery means for actuating said pump means in accordance with said selected supplemental prescription schedule, wherein said pulp means causes a fixed volumetric dosage of medication to be delivered with each pump means actuation.

62. The apparatus of claim 61, wherein each of said supplemental subscription schedules includes a pre-programmed time delay between selection of the particular supplemental subscription schedule and initiation of actual medication delivery.

63. The apparatus sof claim 61 further comprising:

a running integral dosage limiting means for creating and updating a current time window of preselected length, for determining the amount of medication delivery by said medication infusion apparatus within said current time window of preselected length and for inhibiting actuation of said pump means while said determined amount exceeds a running integral dosage limit.

64. A medication infusion apparatus having a controller to actuate a pump means, said controller comprising:

a memory means for storing a basal prescription program, said basal prescription program automatically requesting basal delivery of medication to change to preset rates at pre-programmed intervals during a significant periodic physiologic cycle;

a basal delivery means operably coupled to said memory means and said pump means for actuating said pump means in accordance with said basal prescription program, thereby generating a programmed basal dosage profile; and, a running integral dosage limiting means for creating and updating a current time window of preselected length, for determining the amount of medication delivery sequenced by said basal delivery means within said current time window of preselected length, and for inhibiting pump means actuation while said determined amount exceeds a running integral dose limit.

65. A programmable medication infusion apparatus for providing medication to the living body of a patient, comprising:

an assembly for implantation within a living body, said assembly including;

a medication reservoir for storing selected medication, a pump means for infusing said selected medication stored in said medication reservoir into said living body, a memory means for storing supplemental prescription schedules and at least one basal prescription schedule, each of said supplemental prescription schedules comprising a program to sequence pump actuation over preselected time intervals, and said at least one basal prescription schedule comprising a program to sequence pump means actuation at a basal delivery rate;

a basal delivery means for actuating said pump in accordance with said at least one basal prescription, schedule;

a communication means for receiving a signal carrying programming information;

a supplemental command means responsive to said programming information received by said communication means for selecting a particular supplemental prescription schedule from said memory means; and a supplemental delivery means responsive to said supplemental command means for actuating said pump means in accordance with said selected supplemental prescription schedule, wherein said pump means causes a fixed volumetric dosage of medication to be delivered with each pump actuation; and, an external patient programming means, external to said body for transmitting a signal carrying said programming information to said communication means, said programming information including a selection code requesting said supplemental command means to selectively assign a supplemental prescription schedule to said supplemental delivery means.

66. The apparatus of claim 65, further comprising:
a running integral dosasge limiting means for creating and updating a current, shifting time window of preselected length, for determining the amount of medication delivery by said medication infusion system within said current time window of preselected length and for inhibiting actuation of said pump means while said determined amount exceeds a running integral dosage limit.

67. The apparatus of claim 66, wherein each actuation of said pump means delivers a fixed volumetric dosage of medication, and wherein said running integral dosage limiting means includes a means for summing the number of pump means actuations in said current time window, thereby determining the amount of medication delivery in said current time window.

68. The apparatus of claim 66, wherein said running integral dosage limiting means comprises a means for summing the number of pump means actuations occurring in the most recent three-hour time period, and for inhibiting pump actuation if said sum exceeds a three-hour running integral dose limit.

69. The apparatus of claim 60, wherein said running integral dosage limiting means comprises a means for summing the number of pump means actuations occurring in the most recent 24-hour time period, and for inhibiting pump actuation if said sum exceeds a 24-hour running integral dosage limit.

70. The apparatus of claim 65, further comprising an external physician programming means, external to said body for transmitting a signal carrying a supplemental prescription schedule to said communication means and wherein said communication means further includes a means for storing said received supplemental prescription schedule in said memory means wherein programming information transmitted by said external programming means and received via said communication means includes said at least one prescription schedule and causes said command means to store said at least one prescription schedule in memory.

71. The apparatus of claim 70, wherein said external physician programming means comprises a means for transmitting a signal carrying a running integral dosage limit to said communication means and wherein said communication means comprises a means for programming said running integral dosage limiting means with said running integral dosage limit.

72. The apparatus of claim 70, wherein said external physician programming means comprises a means for transmitting a signal carrying a basal program to said communication means and wherein said communication means comprises a means for programming said basal prescription programming means with said received basal program.

73. The apparatus of claim 70 wherein said external physician programming means comprises a means for transmitting a signal carrying a programming code to said communication means, and wherein said communication means comprises a means for ignoring selected programming information transmitted by said external patient programming means in response to said received programming code.

74. The apparatus of claim 70 wherein said external a physician programming means comprises a means for transmitting a signal carrying a selection code to said communication means, and wherein said supplemental command means selects a particular supplemental prescription schedule from said memory for delivery by said supplemental delivery means in response to said received selection code from said physician programming means.

75. The apparatus as in claim 65, wherein each of said supplemental prescription schedule schedules is a sequence of integers with each integer corresponding to the lapse time since that particular supplemental prescription schedule was assigned to said supplemental delivery means, said supplemental delivery means comprises a means for evaluating each integer in sequence and actuating said pump when means actual lapse time equals the lapse time corresponding to that integer presently under evaluation.

76. The apparatus of claim 75, wherein the value of each of said integers corresponds to the number of minutes of lapse time since the particular supplemental prescription schedule was assigned to said supplemental delivery means.

77. The apparatus of claim 65, wherein said at least one basal prescription schedule a sequence of binary bits, each bit corresponding to a fixed time interval, and wherein said basal delivery means comprises a means for evaluating each bit in sequence moving from the present bit to the next bit each fied time interval, and for actuating sai pump if the current bit is active.

78. The apparatus of claim 77, wherein said basal program is a sequence of binary bits, each bit representing a quarter-hour lapse time, wherein said delivery means will actuate the pump means during a particular quarter-hour, if the sequence bit corresponding to that particular quarter-hour lapse time is active.

79. The apparatus of claim 65, wherein said communication means further comprises a handshaking means for verifiying programming information transmitted by said patient programming means, wherein said handshaking means comprises a means for transmitting to said external programming means the received programming information, said external programming means comprising a means for receiving and verifying said received programming information and for transmitting an execution code, said handshaking means further comprising a means for evaluating a selection code received by said communication means to determine if a valid execution code was received in a timely fashion said handshaking means comprises a means for instructing said supplemental command means to perform the requested selection code.

80. The apparatus of claim 65, wherein said external patient programming means comprises a means for transmitting programming information containing a basal adjustment code to said communication means, said basal adjustment code requesting adjustment of the amplitude of said variable basal delivery profile, and wherein said basal delivery means further comprises a means operably coupled to said communication means for adjusting the amplitude of said variable basal delivery profile for a certain time period in accordance with said received basal adjustment code.

81. The apparatus of claim 80, wherein said basal adjustment code requests half or full delivery of said basal delivery profile.

82. The apparatus of claim 81, further comprising a data recording means for recording the number of times said communication means receives said basal adjustment code requesting half or full basal delivery.

83. The apparatus of claim 80, wherein said external patient programming means includes a means for transmitting an inhibit command for inhibiting pump means actuation for a certain set period of time and wherein said basal delivery means further comprises a means operably coupled to said communication means for inhibiting pump means actuation for said set period of time in response to said inhibit command.

84. The apparatus of claim 83, further comprising a data recording means for recording the number of times said communication means receives said inhibit command.

85. The apparatus of claim 65, wherein said external patient programming means comprises a means for transmitting programming information containing a countermand code to said communication means, wherein said command means further comprises a means associated with said basal delivery means and said supplemented delivery means for countermanding the most recent programming information entry in response to said received countermand code.

86. The apparatus of claim 85, further comprising a data recording means for recording the number of times said communication means receives said countermand code.

87. The apparatus of claim 65, wherein said supplemental command means further comprises a means for checking an assigned supplemental prescription schedule for errors and for alerting said patient to such errors.

88. The apparatus of claim 65 comprising an incremental integrating rate limiting means for inhibiting pump means actuation when a certain maximum dosage envelope is exceeded.

89. The apparatus of claim 65 further comprising an incremental integrating rate limiting means, said incremental integrating rate limiting means comprising:
  a pump means monitoring means for providing a pulse each time said pump means delivers a certain volumetric dosage of medication,
  a clock capable of delivering N pulses per hour; and,
  an updown counter capable of storing M counts, operably connected to said clock and said pump means monitoring means, said updown counter initially set at M counts, each pulse from said pump means monitoring means reducing said updown counter by one count, each pulse from said clock increasing said updown counter by one count up to the maximum M counts, and wherein said updown counter includes a means for inhibiting pump means actuation when the count in said updown counter is zero.

90. The appapatus of claim 89, wherein said pump means monitoring means provides a pulse each time said pump means is activated.

91. The apparatus of claim 89, further comprising an external physician programming means, external to said body for transmitting a code to said communication means setting the storage capacity (M) of said updown counter to a value and wherein said communication means further includes a means operably coupled to said incremental integrating rate limiting means for programming the storage capacity (M) of said updown counter in accordance with said received code.

92. The apparatus of claim 89, further comprising an external physician programming means, external to said body for transmitting a code to said communication means setting the pulse per hour rate (N) of said clock to a value and wherein said communicaton means further includes a means operably coupled to said incremental integrating rate limiting means for programming the pulse per hour (N) rate of said clock in accordance with said received code.

93. The apparatus of claim 65 further comprising a data recording means included within said assembly adapted for implantation and operably connected to said supplemental command means, said basal prescription programming means and said communication means for recording utilization data nad monitoring and recording performance of said medication infusion system.

94. The apparatus of claim 93, further comprising an external physician programming means, external to said body for transmitting a code from said external programming means to said communication means requesting a dump of recorded data, and wherein said communication menas further includes a means operably coupled to said data recording means for transmitting data recorded by said data recording means in response to said received code.

95. The apparatus of claim 93, wherein said data recording means comprises a means for recording the number times said basal delivery means and said supplemental delivery means request an actuation of said pump means.

96. The apparatus of claim 93, wherein said data recording means comprises a means for recording the number of times programming information specifies a particular selection code.

97. The apparatus of claim 93, wherein said data recording means comprises a verification means for comparing a received selection code with all possible allowed selection codes and further comprises a means for recording the number of unverifiable selection codes, received by said communication means.

98. The apparatus of claim 93, wherein said data recording menas further comprises a means for monitoring and recording the extent of reservoir fill.

99. The apparatus of claim 93, wherein said data recording means further comprises a means for monitoring and recording actual pump means operation.

100. The apparatus of claim 93, wherein said data recording means further comprises a means for monitoring medication infusion outflow.

101. The apparatus of claim 93, wherein said data recording means further comprises a means for monitoring and recording moisture in various parts of said medication infusion system.

102. The apparatus of claim 65, wherein said communication means further comprises an operator error determining means for actuating an alarm means when an incorrect selection code is received.

103. The apparatus of claim 102, wherein said alarm means is included in said assembly adapted to be implanted and generates a subcutaneous electrical stimulation.

104. The apparatus of claim 102, wherein said alarm means generates an audio alarm.

105. The apparatus of claim 102, wherein said operator error determining means comprises a means for actuating said alarm means when said supplemental command means attempts to assign a supplemental prescription schedule having a format error.

106. The apparatus of claim 102, wherein said operator error determining means comprises a means for actuating said alarm means when programming information transmitted by said external patient programming means contains codes requesting particular operations.

107. The apparatus of claim 106 further comprising an operator error determining means for actuating said alarm means when said communication means receives said basal adjustment code requesting half basal rate.

108. The apparatus of claim 107, wherein said operator error determining means comprises a means for actuating said alarm means when said communication means receives said basal adjusting code requesting a return to a full basal rate delivery.

109. The apparatus of claim 106, further comprising an operator error determining means for actuating said alarm means when said communication means receives said inhibit command.

110. The apparatus of claim 106, further comprising an operator error determining means for actuating said alarm means when said communication means receives said countermand code.

111. The apparatus of claim 102, further comprising an external physician programming means, external to said body, for transmitting a code to said communication means requesting that said operator error determining means disregards certain types of anomalies, and wherein said communication means comprises a means operably coupled to said operator error determining means for causing said operator error determining means to disregard certain types of an anomalies in response to said received code.

112. A medication infusion apparatus having a controller to actuate a pump means, said controller comprising:
a memory means for storing a basal prescription program, said basal prescription program automatically requesting basal delivery of medication to change to preset rates at pre-programmed intervals during a significant periodic physiological cycle;
a basal delivery means operably coupled to said memory means in accordance with said basal prescription program, thereby generating a programmed basal dosage profile; and,
a running integral dosage limiting menas for creating and updating a current time window of preselected length, for determining the amount of medication delivery by said medication infusion apparatus within said current time window of preselected length and for inhibiting actuation of said pump means while said determined amount exceeds a running integral dosage limit.

* * * * *